United States Patent
Cheung

(10) Patent No.: US 12,347,528 B2
(45) Date of Patent: Jul. 1, 2025

(54) SYSTEM AND METHOD FOR STORING AND TRANSPORTING DIVERSE GENOMIC DATA

(71) Applicant: KONINKLIJKE PHILIPS N.V., Eindhoven (NL)

(72) Inventor: Yee Him Cheung, Boston, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/917,279

(22) PCT Filed: Mar. 31, 2021

(86) PCT No.: PCT/EP2021/058393
§ 371 (c)(1),
(2) Date: Oct. 6, 2022

(87) PCT Pub. No.: WO2021/204616
PCT Pub. Date: Oct. 14, 2021

(65) Prior Publication Data
US 2023/0207069 A1    Jun. 29, 2023

Related U.S. Application Data

(60) Provisional application No. 63/069,774, filed on Aug. 25, 2020, provisional application No. 63/006,514, filed on Apr. 7, 2020.

(51) Int. Cl.
*G16B 50/50*    (2019.01)

(52) U.S. Cl.
CPC .................................. *G16B 50/50* (2019.02)

(58) Field of Classification Search
CPC ...................................................... G16B 50/50
See application file for complete search history.

(56) References Cited

U.S. PATENT DOCUMENTS

2013/0338934 A1\* 12/2013 Asadi ..................... G16B 30/00
702/20
2017/0124254 A1\* 5/2017 van Rooyen ....... H01L 27/0207
(Continued)

OTHER PUBLICATIONS

Shubham Chandak (Stanford) et al, Proposal of a Unified File Format for the Coding of Genomic Annotations, , Jan. 2020, ISO/IEC JTC1/SC29/WG11. (Year: 2020).\*

(Continued)

*Primary Examiner* — Tony Wu

(57) ABSTRACT

A method (100) for packaging genomic data within a file structure, the method comprising: (i) receiving (110) a genomic dataset comprising genomic data; (ii) extracting (120) a plurality of attributes from the genomic dataset, wherein each of the plurality of attributes is defined within an attribute information table of the data structure; (iii) breaking (130) each attribute into a plurality of chunks of a predetermined size; (iv) indexing (140) each of the plurality of chunks in the master index of the data structure; (v) compressing (150) each of the plurality of chunks individually; and (vi) packaging (160) each compressed chunk within an allocated location as defined by the master index; wherein the data structure is configured such that each of the plurality of chunks can be decompressed individually.

13 Claims, 12 Drawing Sheets

(56) References Cited

U.S. PATENT DOCUMENTS

2020/0051667 A1     2/2020   Alberti
2020/0051668 A1     2/2020   Zoia

OTHER PUBLICATIONS

International Search Report and Written Opinion from PCT/EP2021/058393 mailed Jul. 9, 2021.

Shubham Chandak (Stanford) et al: Proposal of a Unified File Format for the Coding of Genomic Annotations, 129. MPEG Meeting; Jan. 13, 2020 Jan. 17, 2020; Brussels; (Motion Picture Expert Group or ISO/IEC JTC1/SC29/WG11).

Horlova et al: "Multi-Dimensional Genomic Data Management for Region-Preserving Operations", 2019 IEEE 35th International Conference on Data Engineering (ICDE), IEEE, Apr. 8, 2019 (Apr. 8, 2019), pp. 1166-1177.

\* cited by examiner

| Column A | Column B | Column C |
|----------|----------|----------|
| $x_{00}$ | $y_{01}$ | $z_{02}$ |
| $x_{10}$ | $y_{11}$ | $z_{12}$ |
| ⋮ | ⋮ | ⋮ |
| $x_{n0}$ | $y_{n1}$ | $z_{n2}$ |

FIG. 2A

| Column A | Column B | Column C |
|----------|----------|----------|
| $x_{00}; y_{00}; z_{00}$ | $x_{01}; y_{01}; z_{01}$ | $x_{02}; y_{02}; z_{02}$ |
| $x_{10}; y_{10}; z_{10}$ | $x_{11}; y_{11}; z_{11}$ | $x_{12}; y_{12}; z_{12}$ |
| ⋮ | ⋮ | ⋮ |
| $x_{n0}; y_{n0}; z_{n0}$ | $x_{n1}; y_{n1}; z_{n1}$ | $x_{n2}; y_{n2}; z_{n2}$ |

FIG. 2B

Table Data Block

Type 0: Chunk-Contiguous, includes chunk indices
Type 1: Attribute-Contiguous, includes attribute ID

| Payload Size [0] | Payload [0] |
| --- | --- |
| ⋮ | |
| Payload Size [$n$] | Payload [$n$] |

FIG. 7

| Box key (with hierarchical level) | | | | | | Scope | Mandatory |
|---|---|---|---|---|---|---|---|
| 0 | 1 | 2 | 3 | 4 | 5 | | |
| flhd | | | | | | File | * |
| dgcn | | | | | | File | * |
| | dghd | | | | | | * |
| | dgmd | | | | | | |
| | dgpr | | | | | | |
| | dmtl | | | | | Transport | * |
| | dtcn | | | | | File | * |
| | | dthd | | | | | * |
| | | pars | | | | | * |
| | | dtmd | | | | | |
| | | dtpr | | | | | |
| | | dmtb | | | | Transport | * |
| | | tbcn | | | | File | * |
| | | | tbhd | | | | * |
| | | | tbmd | | | | |
| | | | tbpr | | | | |
| | | | tdcn | | | File | * |
| | | | | tdai | | | * |
| | | | | | table_data_header | Transport | * |

FIG. 8A

| Box key (with hierarchical level) | | | | | | Scope | Mandatory |
|---|---|---|---|---|---|---|---|
| 0 | 1 | 2 | 3 | 4 | 5 | | |

Continued from FIG. 8A

| 0 | 1 | 2 | 3 | 4 | 5 | Scope | Mandatory |
|---|---|---|---|---|---|---|---|
| | | | | | tdap | | * |
| | | | | tdmi | | | * |
| | | | | | table_data_header | Transport | * |
| | | | | | tdcs | | * |
| | | | | | tdbo | File | * |
| | | | | tdsi | | | |
| | | | | | table_data_header | Transport | |
| | | | | | tdsd | | |
| | | | | tdbl | | | * |
| | | | | | table_data_header | Transport | * |
| | offset | offs | | | | File | |
| packet | | | | | | Transport | * |
| | packet_header | | | | | Transport | * |

FIG. 8B

SYSTEM AND METHOD FOR STORING AND TRANSPORTING DIVERSE GENOMIC DATA

CROSS REFERENCE TO RELATED APPLICATIONS

This application is a U.S. national phase application of International Application No. PCT/EP2021/058393 filed Mar. 31, 2021 which claims the benefit of U.S. Provisional Applications 63/006,514 filed Apr. 7, 2020 and 63/069,774 filed Aug. 25, 2020 and are incorporated herein by reference.

FIELD OF THE DISCLOSURE

The present disclosure is directed generally to methods and systems for storing and transmitting large quantities of data and, in particular, to the storage, compression, and transmission of genomic data.

BACKGROUND

High-throughput genomic sequencing (HTS) is an important tool for genomics research, and has numerous applications for discovery, diagnosis, and other methodologies. Often, the results of HTS are processed further to obtain higher-level information. The process of aggregating information deduced from single reads and their alignments to the genome into more complex results is generally known as secondary analysis. In most HTS-based biological studies, the output of secondary analysis is usually represented as different types of annotations associated to one or more genomic intervals on the reference sequences.

Indeed, biological studies typically produce genomic annotation data such as mapping statistics, quantitative browser tracks, variants, genome functional annotations, gene expression data and Hi-C contact matrices. These diverse types of downstream genomic data are currently represented in different formats such as VCF, BED, WIG, and many, many more. These formats typically comprise loosely defined semantics, which leads to issues with interoperability, the need for frequent conversions between formats, difficulty in the visualization of multi-modal data, and complicated information exchange, among other issues.

Additionally, the lack of a single format for diverse types of genomic annotation data has stifled work on compression algorithms and has led to the widespread use of general compression algorithms with suboptimum performance. These algorithms do not exploit the fact the annotation data typically comprises of multiple fields (attributes) with different statistical characteristics and instead compress them together. Therefore, while these algorithms support efficient random access with respect to genomic position, they do not allow extraction of specific fields without decompressing the entire file.

SUMMARY OF THE DISCLOSURE

There is a continued need for a unified data format for the efficient representation and compression of diverse genomic annotation data for file storage and data transport. A unified data format would reduce the cost of data storage, improve the speed of data access and processing, provide support for data security and privacy in selective genomic regions, and create improved linkages across different types of genomic annotation and sequencing data, among other advantages.

The present disclosure is directed to inventive methods and systems for storing genomic data within a data structure while enabling access to stored data. Various embodiments and implementations herein are directed to a system or method that receives genomic data. The genomic data can be any of a wide variety of different genomic data types, including but not limited to genomic variants (VCF), gene expressions, genomic functional annotations (e.g., BED, GTF, GFF, GFF3, GenBank, etc.), quantitative browser tracks (e.g., Wig, BigWig, BedGraph, etc.), and/or chromosome conformation capture (e.g., HiC files, etc.), among many others. The system extracts a plurality of attributes from the genomic dataset, and then breaks each attribute down into a plurality of chunks of a predetermined size. The chunks are indexed in the master index of the data structure, with lookup data for each of the plurality of chunks. Each chunk is individually compressed with a compression algorithm, and is then stored within the allocated location of a chunk structure data of the data structure. Thus, the data structure is configured such that each of the plurality of chunks can be decompressed individually. Further, the data structure is configured such that the genomic data type, the attributes, chunk size, and the compression algorithm can each be modified without changing the file structure of the data structure.

Generally, in one aspect, a method for packaging genomic data within a file structure is provided. The method includes: (1) receiving a genomic dataset comprising genomic data of one of a plurality of different types of genomic data; (ii) extracting a plurality of attributes from the genomic dataset, wherein each of the plurality of attributes is defined within an attribute information data structure; (iii) breaking each attribute into a plurality of chunks of a predetermined size, wherein the predetermined size of a chunk is defined within a master index of the data structure; (iv) indexing each of the plurality of chunks in the master index of the data structure, the master index comprising lookup data for each of the plurality of chunks; (v) compressing, with transform and compression algorithms, each of the plurality of chunks individually; and (vi) packaging each compressed chunk within an allocated location within a table block of the data structure, as defined by the master index; wherein the data structure is configured such that each of the plurality of chunks can be decompressed individually; and wherein for each of the genomic data type, the definition of attributes, the definition of chunk size, the transform and compression algorithms, and the organization of chunks can be modified without changing the file structure.

According to an embodiment, a symmetry mode of data for each of the genomic data types can be modified without changing the file structure.

According to an embodiment, the plurality of attributes are one-dimensional attributes, two-dimensional attributes, or a combination thereof, and the parameters of the plurality of attributes and the associated transform and compression algorithms are defined by a uniform interface consisting of Attribute Information, Attribute Parameter Set, and Compressor Parameter Set data structures.

According to an embodiment, a Compressor Parameter Set definition can enable: a sparse transform configured to convert a data matrix into streams of coordinates and values only of entries with non-default values; an attribute-dependent transform requiring values of one or multiple attributes; and application of a single or a cascade of compression algorithms with their corresponding parameters.

According to an embodiment, the data structure further comprises one or more annotation tables representing data at multiple resolutions or time points; a main attribute group; and one or more auxiliary attribute groups comprising different functional classes and populated with auxiliary data, the auxiliary data comprising additional attributes or additional information about the extracted plurality of attributes in a main attribute group.

According to an embodiment, the data structure further comprises a supplementary index configured to facilitate query by values of specific attributes.

According to an embodiment, chunks are organized within the annotation access units of the file structure based on the extracted plurality of attributes, wherein grouping and/or ordering of the with the grouping and ordering of the chunks is customizable through variables such as attribute_contiguity and column_major_chunk_order.

According to an embodiment, the method further includes transporting the file structure after said transform, compression, and packaging steps, and further comprising the step of storing the transported file structure at a receiver.

According to an embodiment, each chunk is a region of an annotation table corresponding to a specific range of rows and/or columns of the annotation table.

According to an embodiment, one or more of the plurality of attributes, the predetermined size of the plurality of chunks, and the associated transform and compression algorithms for each attribute is determined by a user or a software algorithm.

According to another aspect is a system for packaging genomic data. The system includes: a genomic dataset comprising genomic data of one of a plurality of different types of genomic data; a data structure configured to store genomic data; a data compression algorithm; and a processor configured to: (i) extract a plurality of attributes from the genomic dataset, wherein each of the plurality of attributes is defined within an attribute information table of the data structure; (ii) break each attribute into a plurality of chunks of a predetermined size, wherein the predetermined size of a chunk is defined within a master index of the data structure; (iii) index each of the plurality of chunks in the master index of the data structure, the master index comprising lookup data for each of the plurality of chunks; (iv) compressing, with a transform algorithm and the data compression algorithm, each of the plurality of chunks individually; and (v) package each compressed chunk within an allocated location within a chunk table of the data structure, as defined by the master index; wherein the data structure is configured such that each of the plurality of chunks can be decompressed individually; and wherein for each of the genomic data type, the definition of attributes, the definition of chunk size, the transform and compression algorithms, and the organization of chucks can be modified without changing either the data structure.

According to another aspect is a method for the reconstruction and presentation of genomic data from compressed data in a file structure system. The method includes: (i) receiving, at a file structure system, a query for attribute data on one or multiple annotation tables based on a criteria comprising a range of rows and columns, a genomic interval, and/or a specific attribute value; (ii) identifying, by the file structure system, rows and/or columns of an annotation table that satisfy the query criteria using indexing data of the file structure system; (iii) identifying, by the file structure system, one or more compressed chunks in the file structure that comprise data of one or more relevant attributes in the identified rows and/or columns of the annotation table; (iv) looking up, in a master index of the file structure system, a location of the identified one or more compressed chunks in the file data structure; (v) decompressing and inverse transforming each of the identified one or more compressed chunks to generate decompressed and inverse transformed attribute data; and (vi) reconstructing and presenting the decompressed and inverse transformed attribute data.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects as discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

FIG. 2A is a schematic representation of a one-dimensional attribute table, in accordance with an embodiment.

FIG. 2B is a schematic representation of a two-dimensional attribute table, in accordance with an embodiment.

FIG. 7 is a schematic representation of a Table Data Block container structure, in accordance with an embodiment.

FIG. 8A is a first portion of data structure and hierarchical encapsulation levels for the representation of genomic annotation data, in accordance with an embodiment.

FIG. 8B is a second portion of data structure and hierarchical encapsulation levels for the representation of genomic annotation data, in accordance with an embodiment.

DETAILED DESCRIPTION OF EMBODIMENTS

The present disclosure describes various embodiments of a system and method for storing genomic data within a data structure. Applicant has recognized and appreciated that it would be beneficial to provide a method and system comprising a unified data format for the efficient representation and compression of diverse genomic annotation data. A genomic data storage system receives a genomic dataset comprising one or more of a plurality of different data types. The system extracts attributes from the genomic dataset, and then breaks each attribute down into smaller pieces of a predetermined size. These smaller pieces can be called, for example, chunks or tiles. These chunks are indexed in the master index of the data structure, with lookup data for each of the plurality of chunks. Each chunk is individually compressed with a compression algorithm, and is then packaged within the allocated location of the chunk in the data structure. Thus, the data structure is configured such that each of the plurality of chunks can be decompressed individually. The data structure is further configured such that the genomic data type, the attributes, chunk size, the compression and transform algorithms, and the organization and ordering of data chunks can each be modified using the same overall file and transport data format.

Figure 1:
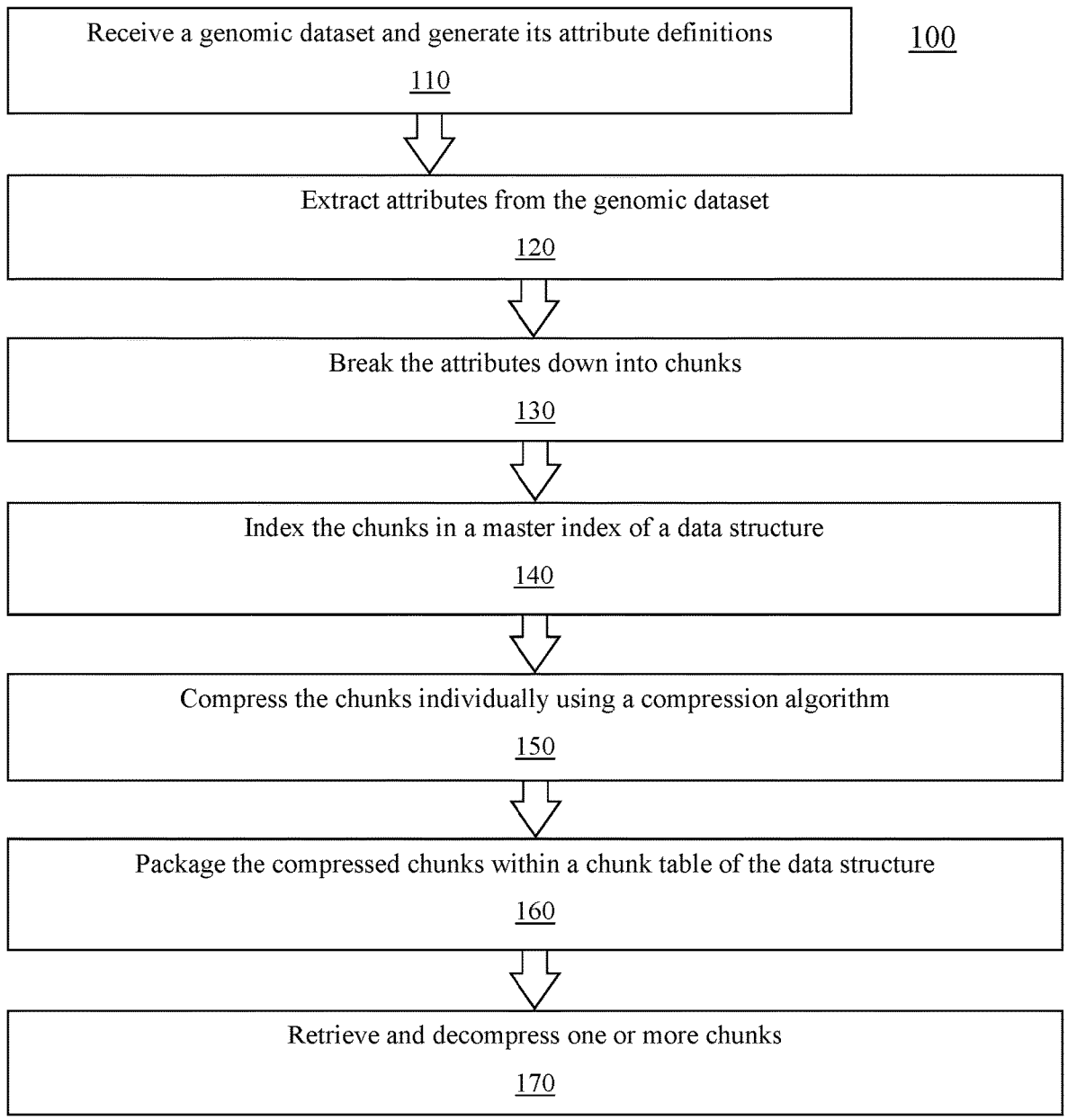
FIG. 1 is a flowchart of a method for packaging genomic data, in accordance with an embodiment.

Referring to FIG. 1, in one embodiment, is a flowchart of a method 100 for packaging genomic data within a data structure using a genomic data storage system. The genomic data storage system may be any of the systems described or otherwise envisioned herein.

At step 110 of the method, the genomic data storage system receives a genomic dataset comprising genomic data of one of a plurality of different types of genomic data. The genomic data can be any of a wide variety of different genomic data types, including but not limited to genomic variants (VCF), gene expressions, genomic functional annotations (e.g., BED, GTF, GFF, GFF3, GenBank, etc.), quantitative browser tracks (e.g., Wig, BigWig, BedGraph, etc.), and/or chromosome conformation capture (e.g., HiC files, etc.), among many others. The received genomic dataset may utilized immediately for additional steps of the methods described or otherwise envisioned herein, or may be stored for future use by this and other methods. Accordingly, the system may comprise or be in communication with local or remote data storage configured to store the genomic dataset.

According to an embodiment, a predefined attribute information template, if available, can be identified for the specific file type and version based on the file extension and information in the file header or metadata. According to another embodiment, a user or programmer of the genomic data storage system can define one or more of the attributes to be extracted and their associated transform and compression algorithms. Alternatively, an algorithm such as a machine learning algorithm can be trained to identify one or more of the attributes to be extracted from the received genomic data, and their associated transform and compression algorithms. Alternatively, a combination of the aforementioned approaches can be used to generate the customized attribute information needed for the parsing, processing and reconstruction of the file. Once the attribute information is defined or otherwise described or identified, the definition or description or identification can be stored within a data structure of a genomic data format. For example, the attribute definition can be stored or otherwise maintained within an attribute information table structure of the data format, where the attribute information table can comprise one or more attribute parameter sets for each of the plurality of identified attributes. Accordingly, the genomic data structure comprises attribute identification and/or definitions for a plurality of different attributes, including for one or more different genomic data types.

At step 120 of the method, the genomic data storage system extracts attributes from the genomic dataset. An attribute can be any data element or characteristic defined by or contained within the data type. For example, attributes of genomic data may be a chromosome number, a position along a chromosome, an RSID, a reference value, a sequencing result, a quality score or value, a gene expression value, a functional annotation, or any of a wide variety of other attributes. This non-exhaustive list is understood not to be limiting, and that attributes can be created and defined as needed. Attributes will depend at least in part on the type of genomic data received or processed by the genomic data storage system.

Referring to FIGS. 2A and 2B, in accordance with an embodiment, are examples of a one-dimensional attribute table (FIG. 2A) and a two-dimensional attribute table (FIG. 2B). Annotation data can comprise, for example, an annotation table or similar data structure. An annotation table can be divided into attributes, each of which may contain data with similar statistical characteristics and can therefore be independently compressed to improve the compression ratio. Usually, an attribute represents a column, but if a column contains multiple data fields, such as the INFO column of a VCF file, then an attribute can represent an individual data field within a column. FIGS. 2A and 2B show two table examples, with $x_{ij}$, $y_{ij}$ and $z_{ij}$ denoting three data fields with different statistical characteristics, where (i, j) are the row and column indices. The table in FIG. 2A can be divided into three one-dimensional (1-d) attributes corresponding to data fields x, y and z. The table in FIG. 2B can be divided into three two-dimensional (2-d) attributes corresponding to the same data fields.

At step 130 of the method, the genomic data storage system breaks attributes into smaller chunks of a predetermined size. To support selective data access, the data of each attribute can be further divided into smaller data pieces known as chunks, each of which can have independent compressor configurations for optimum performance. With a master index that provides the mapping between table indices and chunks, data from selected regions of the table can be accessed by looking up and decompressing only the chunks that overlap with the region without the need to decompress the whole file. According to an embodiment, a user or programmer of the genomic data storage system can define the size of a chunk. Alternatively, an algorithm such as a machine learning algorithm can be trained to determine chunk sizes. According to an embodiment, the predetermined size of a chunk is defined within a master index of the data structure.

Figure 3A:
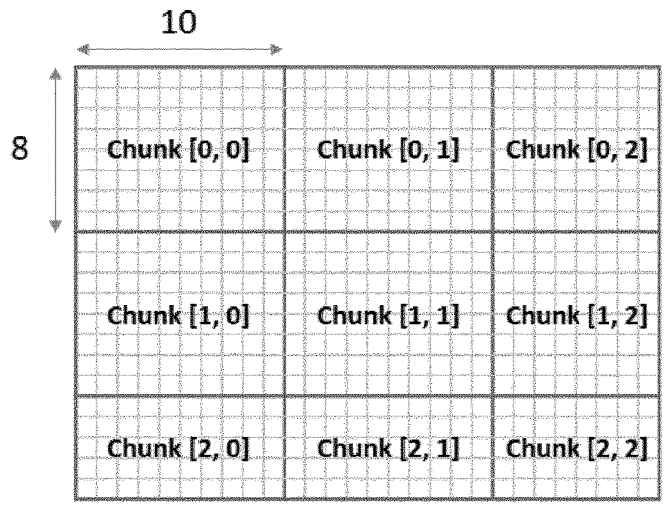
FIG. 3A is a schematic representation of an example chunk structure for uniform-size chunks, in accordance with an embodiment.
Figure 3B:
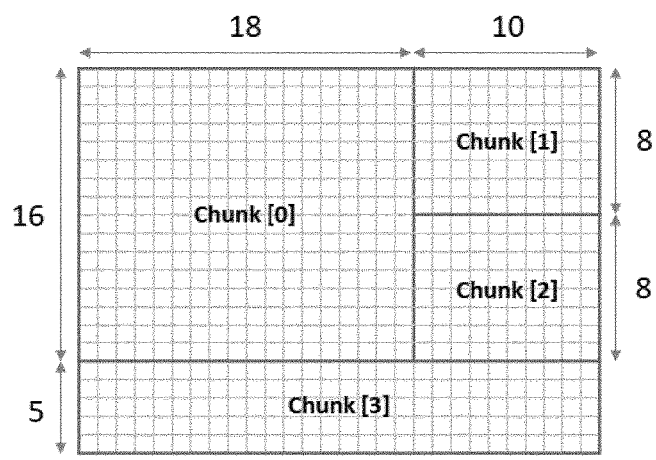
FIG. 3B is a schematic representation of an example chunk structure for variable-size chunks, in accordance with an embodiment.

For example, a chunk can be a rectangular region of a table corresponding to specific ranges of rows and/or columns. Accordingly, the master index may comprise information on how attribute table data should be divided into rectangular chunks. The chunk size, in term of number of rows/columns, can be uniform in which case only the size per dimension needs to be specified, or variable, in which case the ranges of row and/or column indices need to be specified for individual chunks. Often, the same chunk structure is applied to all attributes for ease of indexing. However, in cases where the attributes have widely different characteristics, attribute-dependent chunk structures can be applied. In general, a larger chunk size improves the compression ratio but reduces the speed of selective access. FIG. 3A shows an example chunk structure for uniform-size chunks, and FIG. 3B shows an example chunk structure for variable-size chunks.

At step 140 of the method, the genomic data storage system indexes each of the plurality of chunks in a master index of the data structure. The master index includes lookup data for each of the plurality of chunks. For example, the master index can comprise row and/or column indices that specify individual chunks.

At step 150 of the method, the genomic data storage system compresses each of the plurality of chunks individually and independently using a compression algorithm. The compression algorithm can be any algorithm, method, or process for data transformation and compression. By compressing each chunk individual and independently, data can be more rapidly accessed as small individual chunks can be accessed and decompressed when needed.

At step 160 of the method, the system packages each compressed chunk within an allocated location within a table data block (or "access unit") data structure of the file format, as defined by the master index. Accordingly, the data structure is configured such that each of the plurality of chunks can be decompressed individually.

One of the major benefits of the system and method described or otherwise envisioned herein is that for each of the genomic data types, the definition of attributes, the definition of chunk size, the transform and compression algorithm, and the organization and ordering of data chunks can be modified without changing the file structure.

Accordingly, at step 170 of the method, the genomic data storage system identifies one or more chunks for retrieval, and the location of the one or more chunks, such as via the master index. The system retrieves the identified one or more chunks and decompresses the chunks using their associated decompression and inverse transform algorithms. The decompression and inverse transform algorithms can be any algorithms, methods, or processes for data decompression and inverse transformation.

Genomic Data Storage Structure

The genomic data storage structure in which the received genomic data is packaged may take any of a wide variety of formats. Although a specific format is described with reference to an embodiment, below, it is understood that this is just one example of a data structure that may be utilized by the genomic data storage system described or otherwise envisioned herein.

Figure 4:
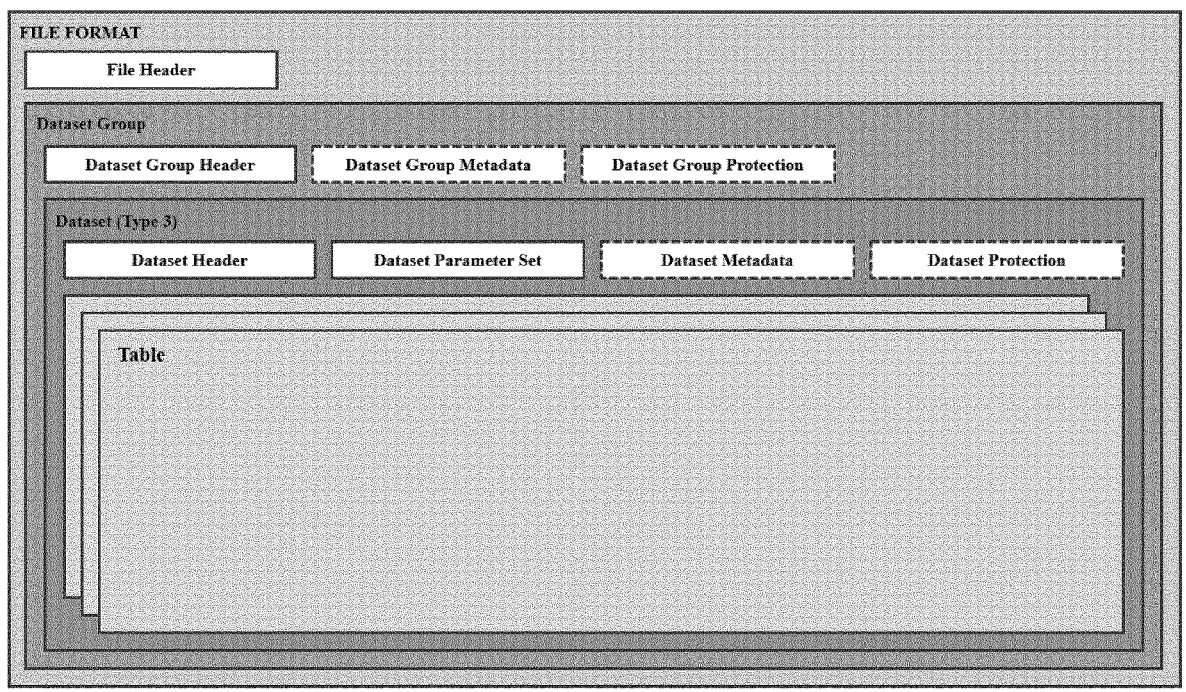
FIG. 4 is a schematic representation of a top-level container hierarchy for an annotation dataset, in accordance with an embodiment.

Referring to FIG. 4 is an embodiment of a top-level container hierarchy for an annotation dataset. In this format, the top-level container boxes of File, Dataset Group, and Dataset as described elsewhere herein are utilized, with extensions to: (1) Dataset to include a new Dataset Type of value 3 for the representation of genomic annotation data, and (2) Dataset Parameter Set to store compressor configurations for use on selected attributes. A dataset can contain multiple (<128) annotation tables, which may correspond to data at different resolutions, sampling time points, etc.

Figure 5:
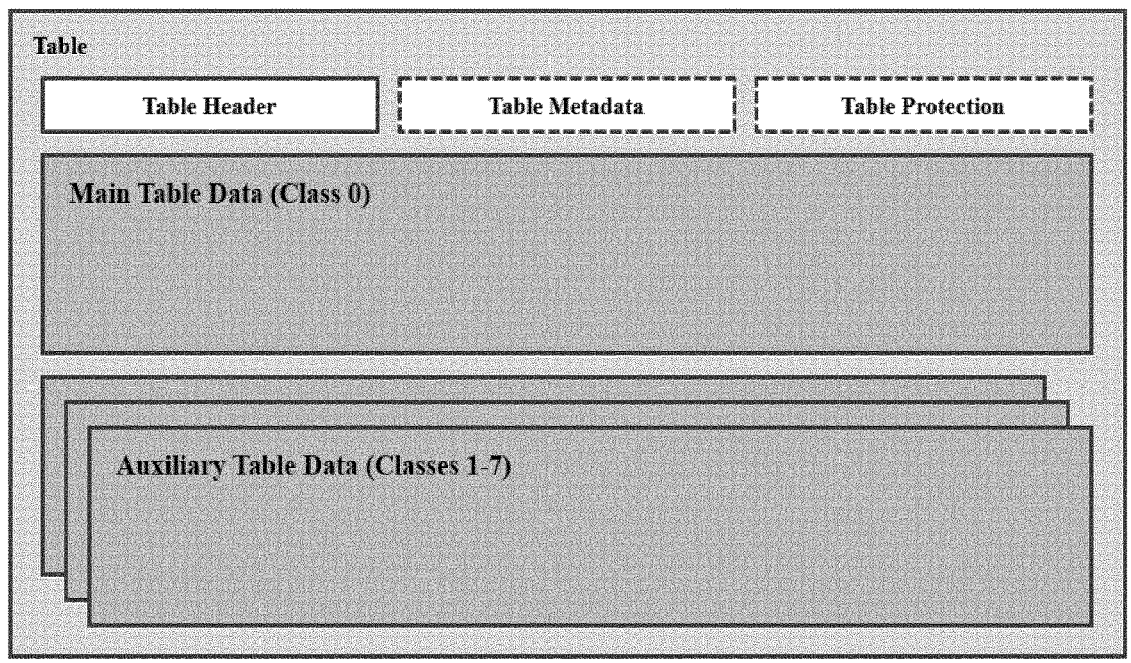
FIG. 5 is a schematic representation of a table container structure, in accordance with an embodiment.

Referring to FIG. 5 is an embodiment of an annotation table container structure. A Table, identified by Table ID, is the main container box that is specific to annotation data and consists of the following components as shown in FIG. 5: (1) Table Header, which is a box describing the content of the Table; (2) Table Metadata, which is an optional box containing metadata associated with the Table, which includes some basic information and metadata that supports functionalities such as data traceability, reproducibility and linkages with other datasets or tables; (3) Table Protection, which is an optional box containing protection information associated with the Table to support confidentiality (encryption), integrity verification (digital signature) and access control policy enforcement; (4) Main Table Data (Class 0), which is a box containing the core attributes of the Table; and (5) Auxiliary Table Data (Classes 1-7), which is one or multiple (<8) optional boxes containing the auxiliary attributes that supplement the Main Table Data. The classes of auxiliary Table Data include: ½ for auxiliary row/column data attributes, ¾ for auxiliary row/column linkage attributes, and 4-7 for user-defined auxiliary attributes.

Figure 6:
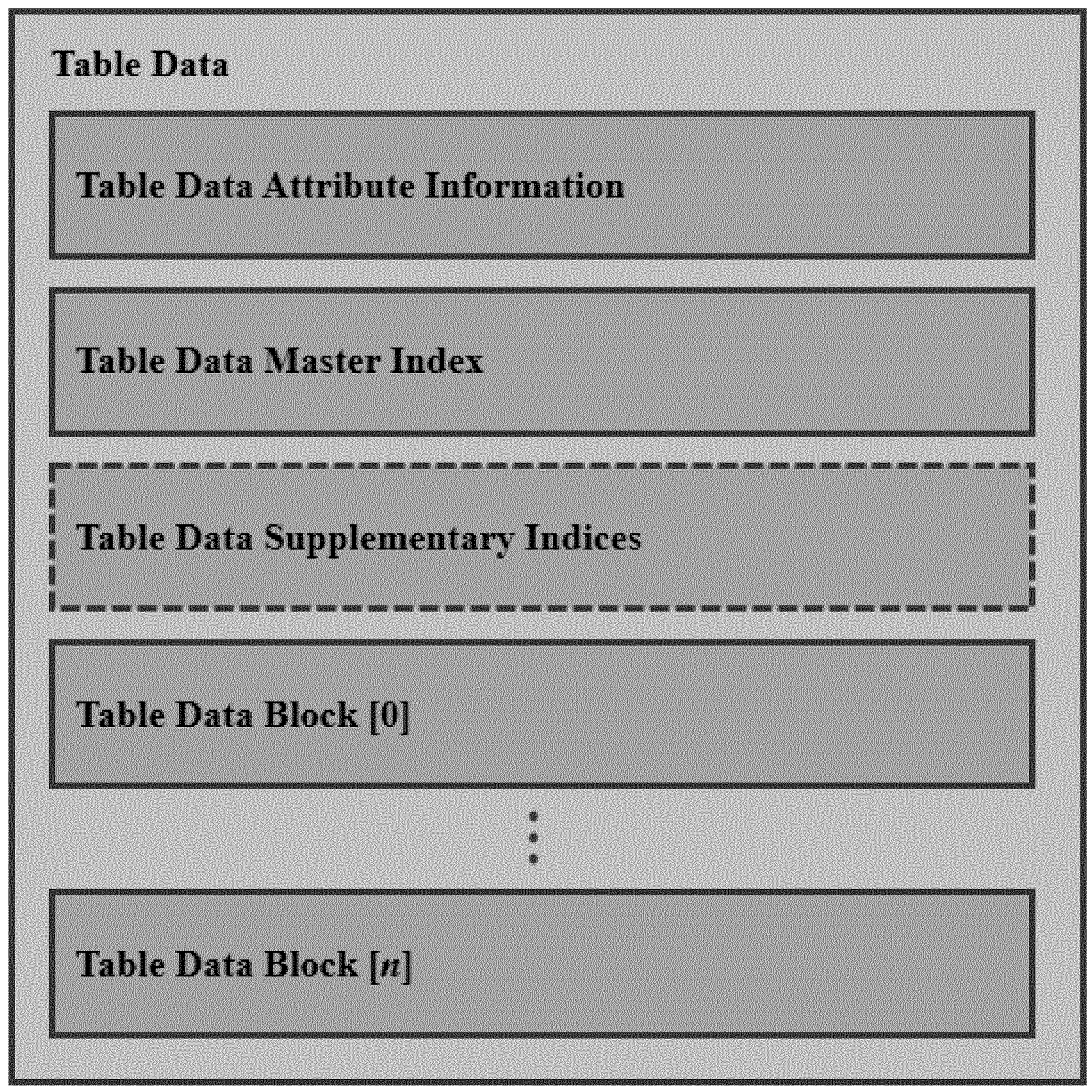
FIG. 6 is a schematic representation of a Table Data container structure, in accordance with an embodiment.

Referring to FIG. 6 is an embodiment of a Table Data (also called an "Attribute Group") container structure. Table Data, identified by Table Data ID, is a container box in Table that groups attributes into classes by their roles, and consists of the following components as shown in FIG. 6: (1) Table Data Attribute Information, which is a box containing a collection of attribute definitions; (2) Table Data Master Index, which is a box containing indexing information that enables the mapping between row and/or column indices of Table Data and specific chunks of an attribute; (3) Table Data Supplementary Indices, which is an optional box containing additional attribute-specific indexing data that enables query search based on criteria such as genomic region, gene symbol or any other attributes; and (4) Table Data Blocks (also called "Annotation Access Units"), which are boxes that groups and organizes the compressed payloads. There are two types of Table Data Block: Type 0 for chunk contiguity, where a block contains payloads of the same chunk ordered by their attribute IDs; and Type 1 for attribute contiguity, where a block contains payloads of the same attribute ordered by their chunk indices. In another embodiment, the Table Data Attribute Information, Table Data Master Index and Table Data Supplementary Indices of the main and auxiliary Table Data structures can be grouped together and placed within the Annotation Table container.

According to an embodiment, a compound query that consists of a logical combination of attribute conditions can be realized by: (1) looking up the row and/or column indices satisfying each attribute condition independently, (2) identifying the subset of indices satisfying the logics in the compound query, (3) mapping the subset of indices to specific chunks of an attribute, and (4) looking up the locations of the payloads of the matching chunks. Other query methods are possible.

Referring to FIG. 7 is an embodiment of a of Table Data Block ("Annotation Access Unit") container structure. The Table Data Block is a container box in Table Data that groups and organizes the compressed payloads. For chunk-contiguous (Type 0) blocks, index (1-d) or indices (2-d) of the chunk to which the payloads belong are included. Whereas for attribute-contiguous (Type 1) blocks, the ID of the attribute to which the payloads belong is included. They are then followed by a concatenation of the size and data of the compressed payloads. The order of the payloads should be the same as the order of the attributes in Table Data Attribute Information for chunk-contiguous blocks, or the order of the chunks for attribute-contiguous blocks. For 2-d Table Data, either row-major or column-major chunk ordering can be applied.

Genomic Data Storage Structure Data Format

The format of the data within the genomic data storage structure may take any of a wide variety of formats. Although a specific format is described with reference to an embodiment, below, it is understood that this is just one example of a data format that may be utilized by the genomic data storage system described or otherwise envisioned herein.

Figure 9:
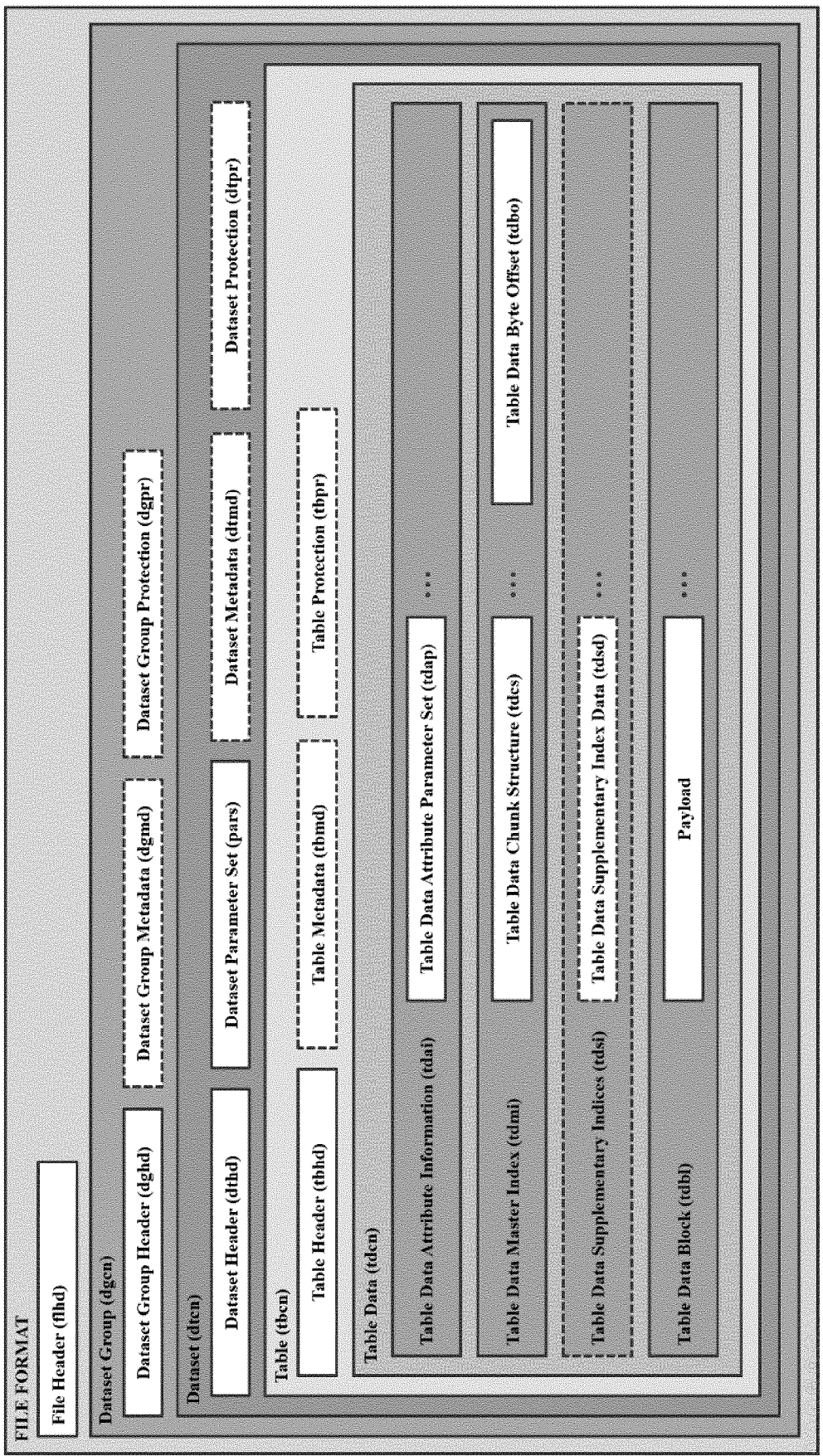
FIG. 9 is a schematic representation of a data structure hierarchy for storage, in accordance with an embodiment.
Figure 10:
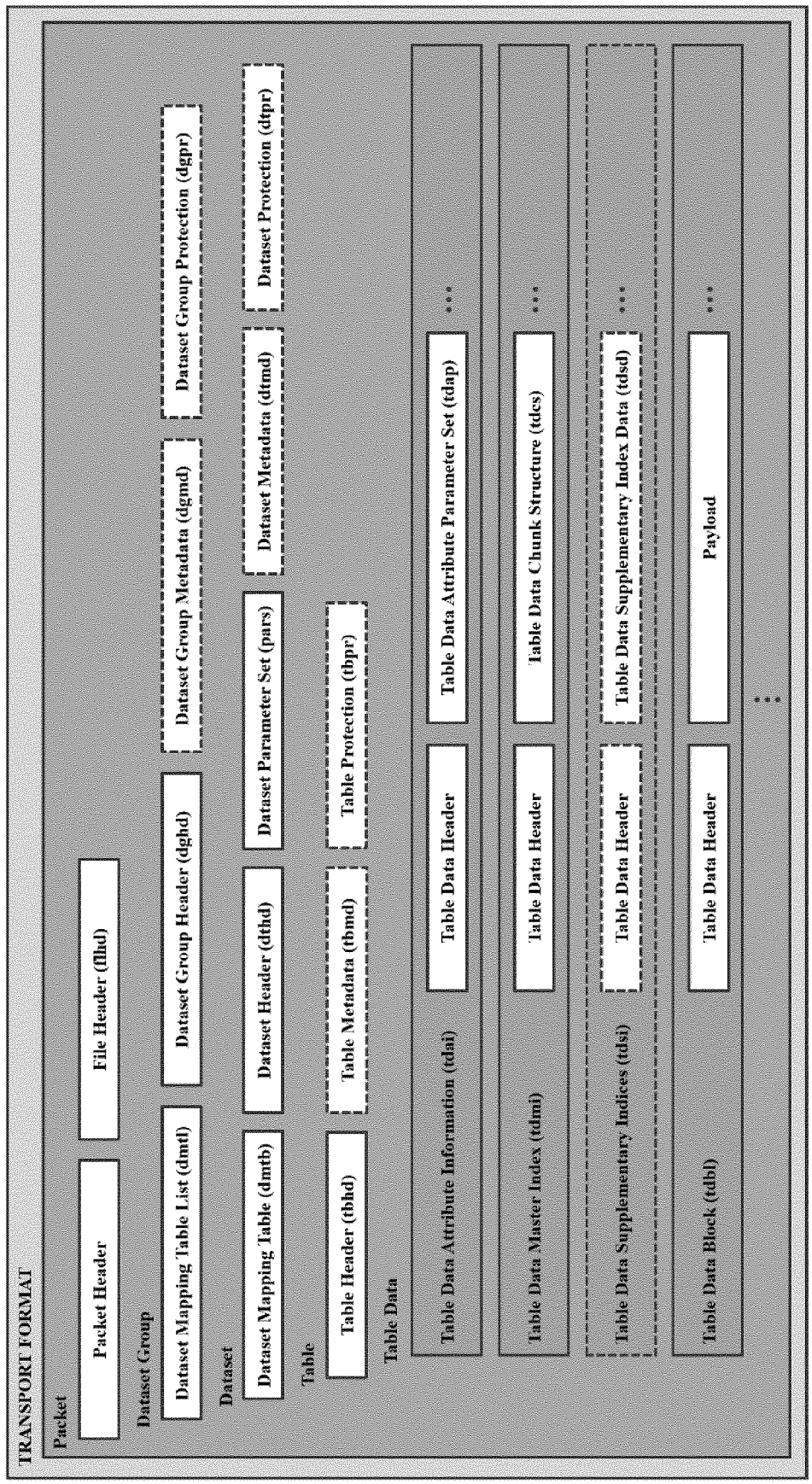
FIG. 10 is a schematic representation of a data structure hierarchy for transport, in accordance with an embodiment.

Referring to FIGS. 8A and 8B (collectively, FIG. 8) is an embodiment of overall data structures and hierarchical encapsulation levels for the representation of genomic annotation data, which are also shown in FIG. 9 (data structure hierarchy for storage) and FIG. 10 (data structure hierarchy for transport). Boxes that may occur at the top-level are shown in the left-most column; indentation is used to show possible containment. Not all boxes need to be used in all files; the mandatory boxes are marked with an asterisk (*) in the Mandatory column: such column refers to the relevant scope (File and/or Transport). Optional boxes are represented with dashed borders in FIGS. 9 and 10. Mandatory boxes are represented with solid borders. When no entry is present in the Scope column, scope is both File and Transport. If the box key is represented in italic format in FIG. 8, the relevant box is represented with neither Key nor Length, but only Value in the gen_info format for all boxes but offset. Individual data fields of the data types—f(n), u(n), st(v), c(n), gen_info and gen_text—are considered an integral part of their containers with the same scope and mandatory statuses, and are therefore not explicitly depicted in FIGS. 9 and 10. In transport format, any box represented in FIG. 10 can be encapsulated in one or more packets. Dataset Group, Dataset, Table and Table Data are represented in FIG. 10 for clarity, but the corresponding container boxes (dgcn, dtcn, tbcn and tdcn) do not exist in transport format.

Box Order

According to an embodiment, in order to improve interoperability, the following rules can be followed for the order of boxes. In file format: (1) The container boxes (Dataset Group, Dataset, Table and Table Data) can be ordered according to the hierarchy specified in FIG. 8; (2) the box order inside the containers dgcn, dtcn, tbcn, and tdcn are specified as described herein; (3) the file header box 'flhd' shall occur before any variable-length box; (4) when present, the offset box 'offs', enables an indirect addressing of boxes, which, while logically respecting the ordering specified in this subclause, may be physically located in a different position in the file; and (5) the contiguity of child boxes inside the containers dgcn, dtcn, tbcn, and tdcn shall not be broken by any box external to the container box, apart from the offset box. In transport format: (1) the box order is not specified, but the dataset mapping table list and dataset mapping table boxes shall be decoded first, and then all other boxes according to the hierarchy specified in FIG. 8; (2) it is strongly recommended to transmit the dataset mapping table list, dataset mapping table and file header boxes first; (3) it is recommended to transmit the boxes in hierarchical order, as specified in FIG. 8; and (4) it is recommended, within Table Data, to transmit Table Data Attribute Information and Table Data Master Index first, before transmitting Table Data Blocks and the optional Table Data Supplementary Indices.

Syntax and Semantics

Table 1 lists the constructs that are used to express the conditions when data elements are present. According to an embodiment, the syntax uses the convention that a variable or expression evaluating to a non-zero value is equivalent to a condition that is true.

TABLE 1

Constructs used to express the conditions when data elements are present.

| Construct | Description |
| --- | --- |
| while (condition) {<br>    data_element<br>    ...<br>} | If the condition is true, then the group of data elements occurs next in the data stream. This repeats until the condition is not true. |
| do {<br>    data_element<br>    ... }<br>while (condition) | The data element always occurs at least once. The data element is repeated until the condition is not true. |
| if (condition) {<br>    data_element<br>    ...<br>} | If the condition is true, then the first group of data elements occurs next in the data stream. |
| else {<br>    data_element<br>    ...<br>} | If the condition is not true, then the second group of data elements occurs next in the data stream. |
| for (i=0; i<n; i++) {<br>    data_element<br>    ...<br>} | The group of data elements occurs n times. Conditional constructs within the group of data elements may depend on the value of the loop control variable i, which is equal to zero for the first occurrence, incremented to 1 for the second occurrence, and so forth. |

As noted, the group of data elements may contain nested conditional constructs. For compactness, the { } are omitted when only one data element follows. Collections of data elements are represented as listed in Table 2.

TABLE 2

Syntax used to represent collections of data elements.

| | |
| --- | --- |
| data_element[ ] | data_element[ ] is an array of data. The number of data elements is indicated by the semantics. |
| data_element[n] | data_element[n] is the (n + 1) th element of an array of data. |
| data_element[m][n] | data_element[m][n] is the (m + 1) th, (n + 1) th element of a two-dimensional array of data. |
| data_element[l][m][n] | data_element[l][m][n] is the (l + 1) th, (m + 1) th, (n + 1) th element of a three-dimensional array of data. |

Bit ordering. The bit order of syntax fields in the syntax tables is specified to start with the most significant bit (MSB) and proceed to the least significant bit (LSB).

Specification of syntax functions. The read bits(n) reads the next n bits from the bitstream and advances the bitstream pointer by n bit positions. When n is equal to 0, read bits(n) is specified to return a value equal to 0 and to not advance the bitstream pointer. The following data types specify the parsing process of each syntax element:

(1) f(n): fixed-pattern bit string using n bits written (from left to right) with the left bit first. The parsing process for this data type is specified by the return value of the function read_bits(n).

(2) u(n): unsigned integer using n bits. When n is "v" in the syntax table, the number of bits varies in a manner dependent on the value of other syntax elements. The parsing process for this data type is specified by the return value of the function read_bits(n) interpreted as a binary representation of an unsigned integer with most significant bit written first.

(3) st(v): null-terminated string encoded as universal coded character set (UCS) transmission format-8 (UTF-8) characters as specified in ISO/IEC 10646. The parsing process is specified as follows: st(v) reads and returns a series of bytes from the bitstream, beginning at the current position and continuing up to but not including the next byte that is equal to 0x00, and advances the bitstream pointer by (stringLength+1)*8 bit positions, where stringLength is equal to the number of bytes returned. The maximum value of stringLength is 16384.

(4) c(n): sequence of n ASCII characters as specified in ISO/IEC 10646.

General Information (gen_info) data structure. KLV (Key Length Value) format is used for all the data structures listed in FIG. 8, except table_data_header, offset, packet and packet_header. The KLV syntax is defined as follows:

```
struct gen_info
{
    c(4)  Key;
    u(64) Length;
    u(8)  Value[ ];
}
```

The Length field specifies the number of bytes composing the entire gen_info structure, including all three fields Key, Length and Value. The table_data_header, offset, packet and packet_header data structures have no Key and no Length, but only Value. All syntax tables, for boxes of type gen_info, represent the internal syntax of the Value[ ] array field only. In the scope of this document the Value[ ] array is referred as just Value.

General Text (gen_text) data structure. The data type gen_text is for the representation of general text in the syntax tables specified in this document, with the option of having the text compressed or not. Its syntax is defined as follows:

```
struct gen_text
{
    u(23) Length;
    u(1)  Compression_Flag;
    u(8)  Data[ ];
}
```

The Length field specifies the number of bytes composing the entire gen_text structure. If Compression_Flag==1, Data[ ] consists of data bytes compressed with the default compressor (Compressor ID==1) defined in dataset_parameter_set. Otherwise, Data[ ] consists of uncompressed characters.

The Dataset structure is extended as described in this section to support a new dataset type, with dataset_type equal to 3, for the representation of genomic annotations. The new dataset type is a collection of annotation tables, where different tables can store the data at multiple resolutions or time points, among other possible applications. The extended Dataset structure allows various genomic annotation data and high-throughput sequencing (HTS) data to be stored in a unified file format, and ensures backward compatibility with ISO/IEC 23092 Series (Second Edition) and interoperability with existing MPEG-G components.

The relevant container box (dtcn in FIG. 8) is mandatory in file format, forbidden in transport format. Child boxes may be present or not, according to the column "Mandatory" in FIG. 8. Child boxes marked with suffix "[ ]" after their name in the Syntax column of Table 3 may be present in multiple instances.

TABLE 3

Dataset Syntax

| Syntax | Key | Type |
|---|---|---|
| dataset { | dtcn | |
|   dataset_header | dthd | gen_info |
|   DT_metadata | dtmd | gen_info |
|   DT_protection | dtpr | gen_info |
|   dataset_parameter_set[ ] | pars | gen_info |
|   if (dataset_type < 3) { | | |
|     /* Same syntax as in Part 1: Table 19 */ | | |
|   } | | |
|   else { | | |
|     For (i=0; i<n_tables; i++) | | |
|       table[i] | tbcn | gen_info |
|   } | | |
| } | | |

Dataset Header is a mandatory box describing the content of a Dataset. This data structure is extended to handle the representation of genomic annotations, with a new dataset_type value of 3. Table 4 comprises dataset header syntax.

TABLE 4

Dataset Header Syntax

| Syntax | Key | Type |
|---|---|---|
| dataset_header { | dthd | |
|   dataset_group_ID | | u(8) |
|   dataset_ID | | u(16) |
|   version | | c(4) |
|   if (version[0..1] == '19') { | | |
|     /* Same syntax as in Part 1: Table 20 */ | | |
|   } | | |
|   else { | | |
|     dataset_type | | u(4) |
|     if (dataset_type < 3) { | | |
|       /* Same syntax as in Part 1: Table 20, except | | |
|         with the data_type row removed */ | | |
|     } | | |
|     else if (dataset_type == 3) { | | |
|       reserved | | u(4) |
|       dataset_subtype | | st(v) |
|       dataset_name | | st(v) |
|       dataset_version | | st(v) |
|       byte_offset_size_flag | | u(1) |
|       n_tables | | u(7) |
|       for (i=0; i<n_tables; i++) { | | |
|         table_ID[i] | | u(8) |
|         table_info[i] | | gen_text |
|       } | | |
|     } | | |
|   } | | |
| } | | |

According to an embodiment are the following dataset header semantics:

dataset_group_ID is the identifier of dataset group containing the dataset including this Dataset Header.

dataset_ID is the identifier of the dataset. Its value shall be one of the dataset_IDs listed in the Dataset Group Header.

version is the combination of version number, amendment number and corrigendum number of ISO/IEC 23092-2 to which the Value field of the dataset, as specified in subclause 0, complies, and is specified as follows:

(1) first two bytes: version number, as the last two digits of the year of release of the major brand (2) third byte: amendment number, as integer counter from 0 to 9, 0 if no amendment yet
(3) fourth byte: corrigendum number, as integer counter from 0 to 9, 0 if no corrigendum yet dataset_type specifies the type of data encoded in the dataset. The possible values are: 0=non-aligned content; 1=aligned content; 2=reference; 3=annotation.

dataset_subtype specifies the type of genomic annotation data encoded in the dataset. The possible values include: "VCF", "GeneExpression", "Wig", "BigWig", "BedGraph", "BED", "GTF", "GFF", "GFF3", "GenBank", "HiC" and other user-defined values. Each dataset_subtype is associated with a set of attribute parameter definitions specific to the corresponding genomic annotation file type.

dataset_name is the name of the dataset, which could be the name of the original annotation file.

dataset_version is the version of the dataset for keeping track of updates to the dataset.

byte_offset_size_flag: if equal to 0, the variable byteOffsetSize used in Table Data Byte Offset, and representing the number of bits used to encode the fields named data_block_byte_offset and payload_byte_offset, is equal to 32; if set to 1, the variable byteOffsetSize is equal to 64.

n_tables specifies the number of tables in the dataset. Multiple tables can be used to store the data at different resolutions, among other possible applications.

table_ID is the identifier of a table unique within the dataset.

table_info stores the general information, e.g. data resolution, on a table.

Dataset Parameter Set

Dataset Parameter Set is a mandatory box describing any of the parameter sets associated to the dataset as specified in subclause 6.5.3.5 of Part 1. While its overall syntax remains the same, its embedded encoding_parameters( ) structure is extended, as described in Tables 4 and 5, to support the definition of compressors needed for the decompression of attributes in the tables of annotation datasets.

TABLE 5

Encoding Parameters Syntax.

| Syntax | Type |
| --- | --- |
| encoding_parameters( ) { | |
|   dataset_type | u(4) |
|   if (dataset_type < 3) { | |
|     /* Same syntax as in Part 2: Table 7 */ | |
|   } | |
|   else { | |
|     reserved | u(4) |
|     n_compressors | u(8) |
|     for (i=0; i < n_compressors; i++) | |
|       compressor[i] | compressor |
|   } | |
| } | |

TABLE 6

Compressor (also called "Compressor Parameter Set") Syntax.

| Syntax | Type |
| --- | --- |
| compressor { | |
|   compressor_ID | st(v) |
|   reserved | u(7) |
|   transform | u(1) |
|   if (transform) { | |
|     transform_algorithm_ID | st(v) |

TABLE 6-continued

Compressor (also called "Compressor Parameter Set") Syntax.

| Syntax | Type |
| --- | --- |
|     n_dependencies | u(8) |
|   } | |
|   n_compression_algorithms | |
|   for (i=0; i<n_compression_algorithms; i++) { | |
|     compression_algorithm_ID[i] | st(v) |
|     compression_algorithm_pars[i] | st(v) |
|   } | |
| } | |

According to an embodiment are the following Dataset Parameter Set semantics:

dataset_type specifies the type of data in the dataset for which the encoding parameters are defined. The possible values are: 0=non-aligned content; 1=aligned content; 2=reference; 3=annotation.

n_compressors specifies the number of compressors, i.e. configurations of transform and compression algorithms, defined for the annotation dataset.

compressor_ID is the unique identifier of the compressor within the dataset, with the values 0 and 1 reserved respectively for no compression and default compressor. It is used in Table Data Attribute Parameter Set to associate the corresponding configuration of transform and compression algorithms with an attribute.

transform is a flag, and if set to 1, indicates that the compressor involves data transform before compression. Otherwise, no data transform is involved.

transform_algorithm_ID is the identifier of the transform algorithm being applied, optionally followed by a comma and then a URI that points to the codes of the transform algorithm. The URI shall be compliant with IETF RFC 3986 and IETF RFC 7320. If the ID is known and the codes are already installed, an MPEG-G compliant software can directly perform the transform/inverse-transform operation. If the ID is unknown and a URI is available, then the software should prompt the user to download and install the codes, and register the ID and a pointer to the executables for future use. If the ID is unknown and there is no URI, then the software should inform the user that the algorithm is not available.

For example, for a sparse transform, where there is a sparse matrix where most entries share the same default value, the matrix can be transformed into the streams of coordinates and values only of entries with non-default values. As another example, for a dependency transform, the values of some attributes might be dependent on the values of other attributes, e.g. genotype likelihoods are related to the genotype call. In such cases, dependency transform can be applied based on the values of one or multiple dependency attributes for improving the compression performance.

n_dependencies specifies the number of dependency attributes for the transform.

n_compression_algorithms specifies the number of compression algorithms applied on an attribute in sequential order.

compression_algorithm_ID[i] is the identifier of the i-th compression algorithm being applied, optionally followed by a comma and then a URI that points to the codes of the compression algorithm. The URI shall be compliant with IETF RFC 3986 and IETF RFC 7320. If the ID is known and the codes are already installed, an MPEG-G compliant software can directly perform the transform/inverse-transform operation. If the ID is unknown and a URI is available, then the software should prompt the user to download and install the codes, and register the ID and a pointer to the executables for future use. If the ID is unknown and there is no URI, then the software should inform the user that the algorithm is not available.

compression_algorithm_pars[i] is a string of parameters in a predefined format required by the i-th compression algorithm.

The following is an example of compressor configurations for the compression of a sparse matrix, such as genotype values or gene expressions:
n_compression_algorithms=3
compression_algorithm_ID={"sparse", "gzip", "7-zip"}
compression_algorithm_pars={"out_streams: coordinates, values",
"in_streams: coordinates",
"in_streams: values"}

According to an embodiment, the compression process is as follows:
(1) Apply the first "sparse" algorithm on the sparse matrix to generate two output streams: "coordinates" and "values" that correspond to the coordinates and values of the cells with non-zero entries,
(2) Apply the second "gzip" algorithm on the "coordinates" stream to generate a stream that consists of the size of type u(32) and payload of the compressed coordinates,
(3) Apply the third "7-zip" algorithm on the "values" stream to generate a stream that consists of the size of type u(32) and payload of the compressed values, and
(4) Output the size and payload of the compressed coordinates, followed by the size and payload of the compressed values.

According to an embodiment, the process can be reversed for decompression:
(1) Extract the compressed coordinates and values payloads with their known sizes,
(2) Decompress the payloads respectively using the "gzip" and "7-zip" algorithms, and
(3) Reconstruct the original sparse matrix from the decompressed coordinates and values.

According to an embodiment, the compressor definitions can also be stored within the Attribute Information data structure in an annotation table.

Table (Also Called "Annotation Table")

According to an embodiment, Table is the main container box of tabulated annotation data and always includes the main Table Data (or main Attribute Group), which contains core attribute data, which can be 1-d (two_dimensional_main==0) or 2-d (two_dimensional_main==1). One or multiple auxiliary Table Data (or auxiliary Attribute Groups) can be included to supplement the main Table Data with attributes associated with the rows/columns for additional data or linkage information, or for other purposes as defined by users.

TABLE 7

| Table Syntax | | |
| --- | --- | --- |
| Syntax | Key | Type |
| table { | tbcn | |
|   table_header | tbhd | gen_info |
|   table_metadata | tbmd | gen_info |
|   table_protection | tbpr | gen_info |
|   table_data_main | tdcn | gen_info |

TABLE 7-continued

| Table Syntax | | |
| --- | --- | --- |
| Syntax | Key | Type |
|   for (i=0; i<n_aux_data; i++) { | | |
|     aux_table_data[i] | tdcn | gen_info |
|   } | | |
| } | | |

According to an embodiment, Table Header is a mandatory box describing the content of a Table.

TABLE 8

| Table Header Syntax | | |
| --- | --- | --- |
| Syntax | Key | Type |
| table_header { | tbhd | |
|   dataset_group_ID | | u(8) |
|   dataset_ID | | u(16) |
|   table_ID | | u(8) |
|   table_info | | gen_text |
|   n_summary_statistics | | u(8) |
|   for (i=0; i<n_summary_statistics; i++) { | | |
|     summary_statistic_key[i] | | st(v) |
|     summary_statistic_value[i] | | st(v) |
|   } | | |
|   reserved | | u(5) |
|   two_dimensional_main | | u(1) |
|   symmetry_mode | | u(3) |
|   symmetry_minor_diagonal | | u(1) |
|   table_index_size | | u(3) |
|   n_aux_data | | u(3) |
|   for (i=0; i<n_aux_data; i++) { | | |
|     aux_data_name[i] | | st(v) |
|     aux_data_metadata[i] | | gen_text |
|   } | | |
| } | | |

According to an embodiment are the following Table Header semantics:

dataset_group_ID is the identifier of dataset group containing the dataset including this Dataset Header.

dataset_ID is the identifier of the dataset. Its value shall be one of the dataset_IDs listed in the Dataset Group Header.

table_ID is the unique identifier of the table within the dataset. Its value shall be one of the table_IDs listed in the Dataset Header.

table_info is the textual information about the table.

n_summary_statistics specifies the number of summary statistics for the table.

(summary_statistic_key[i], summary_statistic_value[i]) is the key-value pair of the ith summary statistic of the table.

two_dimensional_main is a flag, and if set to 1, indicates that all attributes in the main Table Data are 2-d. Otherwise, all attributes in the main Table Data are 1-d.

symmetry_mode specifies the symmetry mode of the main Table Data and is only effective when two_dimensional_main==1. The possible values are: 0=unsymmetrical; 1=symmetrical; 2=skew-symmetric; 3=Hermitian; 4-7=reserved or user-defined. For symmetry modes 1-3, attribute values in the reflected half to the right of the principal/minor diagonal (inclusive of the diagonal if skew-symmetric) should be processed as missing values.

symmetry_minor_diagonal is a flag, and if set to 1, indicates that the symmetry is along the minor diagonal of the main Table Data. Otherwise, symmetry is along the principal diagonal by default.

table_index_size specifies the number of bytes required for representing the row/column index of the table. It determines the size of the fields n_chunks, chunk_size, start_index and end_index in Table Data Chunk Structure.

n_aux_data specifies the number of auxiliary Table Data structures in the Table.

aux_data_name[i] is the name of the ith auxiliary Table Data.

aux_data_metadata[i] is the metadata associated with the ith auxiliary Table Data.

Table Metadata

According to an embodiment, Table Metadata is an optional box containing metadata associated with a Table. In addition to some basic information about the table, it can also contain metadata that supports functionalities such as data traceability, reproducibility and linkages with other datasets or tables.

TABLE 9

Table Metadata Syntax

| Syntax | Key | Type |
| --- | --- | --- |
| table_metadata { | tbmd | |
| dataset_group_ID | | u(8) |
| dataset_ID | | u(16) |
| table_ID | | u(8) |
| TB_metadata_value( ) | | |
| } | | |

According to an embodiment are the following table metadata semantics:

TB_metadata_value( ) contains compressed table metadata. The output of the decoding process is an XML, document with an element Table as root. The XML, schema for table metadata will be provided in a separate document. A table metadata element overwrites the corresponding element whose values differ from the one indicated at the dataset level (i.e., the new value in the table is a specialization of the value at the dataset level). The same approach for metadata protection and mechanism for extensions of the metadata as specified elsewhere herein are applicable to table metadata.

Table Protection

According to an embodiment, Table Protection is an optional box containing protection information associated with a Table to support confidentiality (encryption), integrity verification (digital signature) and access control policy enforcement on selected regions of the Table as required by the user.

TABLE 10

Table Protection Syntax

| Syntax | Key | Type |
| --- | --- | --- |
| table_protection { | tbpr | |
| dataset_group_ID | | u(8) |
| dataset_ID | | u(16) |
| table_ID | | u(8) |
| TB_protection_value( ) | | |
| } | | |

According to an embodiment are the following table protection semantics:

TB_protection_value( ) contains compressed protection metadata. The decoding process to retrieve the XML document from the coded representation is specified herein. It consists of three main components: encryption parameters, privacy policy and digital signatures. Details on the XML schema for table protection metadata will be provided in a separate document.

Controlled access to and authentication of data subsets within a table are enabled through privacy rules and signature elements in the schema. Like the protection metadata at the Dataset Group and Dataset levels, the privacy rules specify who can execute a given action and under which conditions, and the information is conveyed according to the eXtensible Access Control Markup Language (XACML) Version 3.0 specification. Users may define the attributes, chunks, genomic regions, and ranges of table indices on which a privacy rule is applied. Any number of XML signature elements can be present in the Table Protection box and shall use a URI to specify the attributes and chunks associated with each signature. Detached, Enveloped and Enveloping signatures are supported. If decryption is required, signature verification shall be performed before decryption.

Table Data (Also Called "Attribute Group")

According to an embodiment, Table Data is a container box that allows Table attributes to be grouped and organized by their roles as: main data, auxiliary data associated with the rows/columns of the main data, auxiliary row/column linkages with other Tables, and any other auxiliary data as defined by users. There are two ways to organize data payloads in Table Data:

(1) If either attribute_dependent_chunks or attribute_contiguity (or AU_by_attribute) equals 1, group data payloads into Table Blocks (or Annotation Access Units) by attribute (block_type==1) and order them by chunk as in the corresponding chunk structure in Table Data Master Index.

(2) Otherwise, group data payloads into Table Blocks by chunk (block_type==0) and order them by attribute as in Table Data Attribute Information. Chunk contiguity is only allowed when the same chunk structure is shared among all attributes and attribute_contiguity is set to 0.

TABLE 11

Table Data Syntax

| Syntax | Key | Type |
| --- | --- | --- |
| table_data { | tdcn | |
| table_data_ID | | u(3) |
| table_data_class | | u(3) |
| two_dimensional | | u(1) |
| column_major_chunk_order | | u(1) |
| for (i=0; i<(two_dimensional + 1); i++) | | |
| dimension_size[i] | | u(table_index_size*8) |

TABLE 11-continued

Table Data Syntax

| Syntax | Key | Type |
|---|---|---|
| attribute_info | tdai | gen_info |
| master_index | tdmi | gen_info |
| supplementary_indices | tdsi | gen_info |
| if (!attribute_dependent_chunks && | | |
| !attribute_contiguity) { | | |
|   block_type = 0 | | |
|   if (variable_size_chunks \|\| !two_dimensional) { | | |
|     for (i=0; i<n_chunks; i++) { | | |
|       if (sizeof(payload_chunk[i]) > 0) | | |
|         table_block_by_chunk[i] | tdbl | gen_info |
|     } | | |
|   } | | |
|   else if (column_major_chunk_order) { | | |
|     for (j=0; j<n_chunks_per_row; j++) { | | |
|       for (i=0; i<n_chunks_per_col; i++) { | | |
|         if (sizeof(payload_chunk[i][j]) > 0) | | |
|           table_block_by_chunk[i][j] | tbdl | gen_info |
|       } | | |
|     } | | |
|   } | | |
|   else { | | |
|     for (i=0; i<n_chunks_per_col; i++) { | | |
|       for (j=0; j<n_chunks_per_row; j++) { | | |
|         if (sizeof(payload_chunk[i][j]) > 0) | | |
|           table_block_by_chunk[i][j] | tbdl | gen_info |
|       } | | |
|     } | | |
|   } | | |
| } | | |
| else { | | |
|   block_type = 1 | | |
|   for (i=0; i<n_attributes; i++) { | | |
|     if (sizeof(payload_attribute[i]) > 0) | | |
|       table_block_by_attribute[i] | tdbl | gen_info |
|   } | | |
| } | | |
| } | | |

According to an embodiment are the following table data semantics:

table_data_ID is the unique identifier of the Table Data within the Table.

table_data_class specifies the class of the Table Data. The possible values are:

0—main Table Data

1—auxiliary Table Data for data attributes mapped to the rows of the main Table Data 2—auxiliary Table Data for data attributes mapped to the columns of the main Table Data 3—auxiliary Table Data for linkage attributes mapped to the rows of the main Table Data 4—auxiliary Table Data for linkage attributes mapped to the columns of the main Table Data 5-7—any auxiliary Table Data defined by the user Within a Table, there can only be one main Table Data of class 0. For auxiliary Table Data of classes 1-4, if the attributes are two-dimensional, the mapping is always between the rows of the auxiliary Table Data and the rows (classes 1 and 3) or columns (classes 2 and 4) of the main Table Data.

two_dimensional is a flag, and if set to 1, indicates that all attributes in the Table Data are 2-d. Otherwise, all attributes in the Table Data are 1-d. For main Table Data, its value should be the same as two_dimensional_main.

column_major_chunk_order (or column_major_tile_order) is a flag only relevant for an attribute when two_dimensional==1 and variable_size_chunks==0 in the corresponding Table Data Chunk Structure. If set to 1, it indicates that the chunks of the attribute within the Table Data Block (block_type==1) are in column-major order. Otherwise, the chunks are in row-major order.

dimension_size[i] specifies the total number of rows (i==0) or columns (i==1) in the Table Data when two_dimensional==1, or simply the number of elements when two_dimensional==0. In the case of transport when data generation is ongoing, a value of 0 can be applied. At the completion of data generation and transport, the value(s) of dimension_size[ ] should be computed and reassigned.

Table Data Attribute Information

According to an embodiment, Table Data Attribute Information is a collection of attribute definitions encapsulated in attribute_parameter_set, with the number of attributes specified in n_attributes.

TABLE 12

Table Data Attribute Information Syntax

| Syntax | Key | Type |
|---|---|---|
| table_data_attribute_information { | tdai | |
|   table_data_header | | table_data_header |
|   n_attributes | | u(16) |
|   for (i=0; i<n_attributes; i++) | | |
|     attribute_parameter_set[i] | tdap | gen_info |
| } | | |

Table Data Attribute Parameter Set

According to an embodiment, Table Data Attribute Parameter Set is a box that contains the definitions of an attribute, including some basic information and configurations of its associated compressor.

TABLE 13

Table Data Attribute Parameter Set Syntax

| Syntax | Key | Type |
|---|---|---|
| table_data_attribute_parameter_set { | tdap | |
|   attribute_ID | | u(16) |
|   attribute_name | | st(v) |
|   attribute_metadata | | gen_text |
|   attribute_type | | u(8) |
|   attribute_default_value | | st(v) |
|   attribute_missing_value | | st(v) |
|   compressor_ID | | u(8) |
|   if (transform) { | | |
|     for (i=0; i<n_dependencies; i++) { | | |
|       reserved | | u(5) |
|       dependency_table_data_ID[i] | | u(3) |
|       dependency_attribute_ID[i] | | u(16) |
|     } | | |
|   } | | |
|   compressor_common_data | | compressor_common_data |
| } | | |

According to an embodiment are the following Table Data Attribute Parameter Set semantics:

attribute_ID is the identifier of the attribute unique within Table Data. It is the same as the index of the attribute in attribute_parameter_set of Table Data Attribute Information.

attribute_name is the name of the attribute.

attribute_metadata is the metadata of the attribute, which can include a description on the meaning and format of the attribute value and its belonging attribute group.

attribute_type specifies the data type of the attribute. The possible values and their respective data type definitions are listed in Table 14.

TABLE 14

Attribute Type Definitions

| attribute_type | Type | Number of bytes |
|---|---|---|
| 0 | Null terminated string | variable |
| 1 | Char | 1 |
| 2 | Boolean | 1 |
| 3 | Uint8 | 1 |
| 4 | Int8 | 1 |
| 5 | Uint16 | 2 |
| 6 | Int16 | 2 |
| 7 | Uint32 | 4 |
| 8 | Int32 | 4 |
| 9 | Uint64 | 8 |
| 10 | Int64 | 8 |
| 11 | Float | 4 |
| 12 | Double | 8 |
| 13 | Start_end (pair of uint32) | 8 | attribute_default_value is the default value of the attribute, mainly used for sparse encoding when most values equal to the default are excluded.

attribute_missing_value is the missing value of the attribute to be used in place of a null value in the output after decompression.

compressor_ID is the ID of one of the compressors defined in Dataset Parameter Set for compressing the data of the attribute.

(dependency_table_data_ID[i], dependency_attribute_ID[i]) correspond to the table ID and attribute ID of the i-th dependency attribute required by the transform algorithm (if transform==1) within the compressor referenced by compressor_ID.

compressor_common_data stores the codebooks/statistical models used by the associated compressor to apply commonly on all chunks.

Table Data Master Index

According to an embodiment, Table Data Master Index is a container box of indexing information that includes the definition of chunk structure(s), i.e. the range of indices (both rows and columns for 2-d data) per chunk, and byte-offset pointers to individual Table Blocks and their subsidiary payloads.

TABLE 15

Table Data Master Index Syntax

| Syntax | Key | Type |
|---|---|---|
| table_data_master_index { | tdmi | |
|   table_data_header | | table_data_header |
|   reserved | | u(6) |
|   attribute_dependent_chunks | | u(1) |
|   attribute_contiguity | | u(1) |
|   if (!attribute_dependent_chunks) | | |
|     chunk_structure | tdcs | gen_info |
|   else { | | |
|     for (i=0; i<n_attributes; i++) | | |
|       chunk_structure[i] | tdcs | gen_info |
|   } | | |
|   payload_byte_offset | tdbo | gen_info |
| } | | |

According to an embodiment are the following Table Data Master Index semantics:

attribute_dependent_chunks is a flag, and if set to 1, indicates that each attribute has a different chunk structure. Otherwise, all attributes share the same chunk structure.

attribute_contiguity (or AU_by_attribute) is a flag, and if set to 1, indicates that the data payloads are grouped into Table Blocks by attribute. Otherwise, data payloads are grouped into Table Blocks by chunk.

Table Data Chunk Structure (Also Called Attribute Data Tile Structure)

According to an embodiment, Table Data Chunk Structure is a box specifying how the 1-d or 2-d attribute data should be divided into rectangular chunks defined by ranges of row and column indices.

TABLE 16

Table Data Chunk Structure Syntax

| Syntax | Key | Type |
|---|---|---|
| table_data_chunk_structure { | tdcs | |
|   reserved | | u(7) |
|   variable_size_chunks | | u(1) |
|   n_chunks | | u(table_index_size*8) |
|   if (variable_size_chunks) { | | |
|     for (i=0; i<n_chunks; i++) { | | |
|       for (j=0; | | |
|       j<(two_dimensional +1); j++) { | | |
|         start_index[i][j] | | u(table_index_size*8) |
|         end_index[i][j] | | u(table_index_size*8) |
|       } | | |
|     } | | |
|   } | | |
|   else { | | |
|     for (j=0; j<(two_dimensional + 1); j++) | | |
|       chunk_size[j] | | u(table_index_size*8) |
|   } | | |
| } | | |

According to an embodiment are the following Table Data Chunk Structure semantics:

variable_size_chunks is a flag, and if set to 1, indicates that the size of each chunk is different, and thus the corresponding start and end indices are specified independently. Otherwise, a uniform size applies to all chunks. If the number of rows/columns is unknown as in the case of data generation and transport, a uniform chunk_size should be applied with variable_size_chunks set to 0.

n_chunks specifies the total number of chunks defined in this chunk structure. In the case of transport when data generation is ongoing, a value of 0 can be applied if the number is unknown. At the completion of data generation and transport, the value of n_chunks should be computed and reassigned. The number of bits for n_chunks is the same as the number of bits for column/row index, i.e. table_index_size*8, to allow having one chunk per row or column.

(start_index[i][j], end_index[i][j]) is the pair of start and end indices defining the range of rows (j==0) or columns (j==1) for the ith rectangular chunk, only used when variable_size_chunks==1.

chunk_size[j] specifies the number of rows (j==0) or columns (j==1) per chunk, only used when variable_size_chunks==0.

Table Data Byte Offset (Also Called Attribute Data Byte Offset)

According to an embodiment, Table Data Byte Offset is a box containing the byte-offset pointers to the Table Data Blocks and their individual payloads.

TABLE 17

Table Data Byte Offset Sytax

| Syntax | Key | Type |
|---|---|---|
| table_data_byte_offset { | tdbo | |
|   if (!attribute_dependent_chunks && | | |
|     !attribute_contiguity) { | | |
|     if (variable_size_chunks || !two_dimensional) { | | |
|       for (j=0; j<n_chunks; j++) { | | |
|         chunk_block_offset[j] | | u(byteOffsetSize) |
|         if (chunk_block_offset[i] > 0) { | | |
|           for (i=0; i<n_attributes; i++) | | |
|             payload_offset[i][j] | | u(byteOffsetSize) |
|         } | | |
|       } | | |
|     } | | |
|     else if (column_major_chunk_order) { | | |
|       for (k=0; k<n_chunks_per_row; k++) { | | |
|         for (j=0; j<n_chunks_per_col; j++) { | | |
|           chunk_block_offset[j][k] | | u(byteOffsetSize) |
|           if (chunk_block_offset[j][k] > 0) | | |
|             for (i=0; i<n_attributes; i++) | | |
|               payload_offset[i][j][k] | | u(byteOffsetSize) |
|         } | | |
|       } | | |
|     } | | |
|     else { | | |
|       for (j=0; j<n_chunks_per_col; j++) { | | |
|         for (k=0; k<n_chunks_per_row; k++) { | | |
|           chunk_block_offset[j][k] | | u(byteOffsetSize) |
|           if (chunk_block_offset[j][k] > 0) { | | |
|             for (i=0; i<n_attributes; i++) | | |
|               payload_offset[i][j][k] | | u(byteOffsetSize) |
|           } | | |
|         } | | |
|       } | | |
|     } | | |
|   } | | |
| } | | |

TABLE 17-continued

Table Data Byte Offset Sytax

| Syntax | Key | Type |
|---|---|---|
| else { <br>  for (i=0; i<n_attributes; i++) { <br>    attribute_block_offset[i] <br>    if (attribute_block_offset[i] > 0) { <br>      if (variable_size_chunks[i] \|\| <br>      !two_dimensional) { <br>        for (j=0; j<n_chunks[i]; j++) <br>        payload_offset[i][j] <br>      } <br>      else if (column_major_chunk_order) { <br>        for (k=0; k<n_chunks_per_row[i]; k++) { <br>          for (j=0; j<n_chunks_per_col[i]; j++) <br>            payload-_offset[i][j][k] <br>        } <br>      } <br>      else { <br>        for (j=0; j<n_chunks_per_col[i]; j++) { <br>          for (k=0; k<n_chunks_per_row[i]; k++) <br>            payload-_offset[i][j][k] <br>        } <br>      } <br>    } <br>  } <br>} | | u(byteOffsetSize) <br><br><br><br><br><br><br>u(byteOffsetSize) <br><br><br><br><br><br><br>u(byteOffsetSize) <br><br><br><br><br><br><br>u(byteOffsetSize) |

According to an embodiment are the following Table Data Byte Offset semantics:

chunk_block_offset[j][k] is the byte offset, counting from the beginning of the associated Table Data container, to a chunk-contiguous Table Data Block (block_type==0) that contains the payload data of all attributes for the chunk of row and column indices (j, k). Its value should be 0 if the Table Data Block for chunk (j, k) does not exist when the payloads are all empty. If variable_size_chunks==1 and two_dimensional==0, the second index [k] can be dropped.

attribute_block_offset[i] is the byte offset, counting from the beginning of the associated Table Data container, to an attribute-contiguous Table Data Block (block_type==1) that contains the payload data of all chunks for the i-th attribute as defined in Table Data Attribute Information. Its value should be 0 if the Table Data Block for the i-th attribute does not exist when the payloads are all empty.

payload_offset[i][j][k] is the byte offset, counting from the beginning of the encapsulating Table Data Block container, to the compressed payload data that corresponds to the chunk of row and column indices (j, k) in the i-th attribute. Note that even for empty payloads, payload_size must be included and set to 0. If variable_size_chunks==1 and two_dimensional==0, the third index [k] can be dropped.

Note that if attribute_dependent_chunks==1, the values of n_chunks[i], n_chunks_per_row[i] and n_chunks_per_col[i] are specific to the i-th attribute. Otherwise, their values are uniform across all attributes and the index [i] can be dropped.

According to an embodiment, described below are data structures specific to the transport of genomic information.

Table Data Supplementary Indices

According to an embodiment, Table Data Supplementary Indices is an optional container box that carries additional attribute-specific indexing data for enabling query search based on criteria such as genomic region, gene symbol or any other attributes.

TABLE 18

Table Data Supplementary Indices Syntax

| Syntax | Key | Type |
|---|---|---|
| table_data_supplementary_indices { | tdsi | |
|   table_data_header | | table_data_header |
|   n_supp_indices | | u(8) |
|   for (i=0; i<n_supp_indices; i++) | | |
|     supp_index_data[i] | | tdsd |
| } | | |

According to an embodiment are the following Table Data Supplementary Indices semantics:

n_supp_indices specifies the number of supplementary indices associated with the Table Data.

Table Data Supplementary Index Data (Also Called Attribute Value Index)

According to an embodiment, Table Data Supplementary Index Data is a box containing information and data of a supplementary index.

TABLE 19

Table Data Supplementary Index Data syntax

| Syntax | Key | Type |
|---|---|---|
| table_data_supplementary_index_data | tdsd | |
| { | | |
|   n_index_attributes | | u(8) |
|   for (i=0; i<n_index_attributes; i++) | | |
|     index_attribute_ID[i] | | u(16) |
|   index_type | | st(v) |
|   index_data | | u(index_data_size*8) |
| } | | |

According to an embodiment are the following Table Data Supplementary Index Data semantics:

n_index_attributes is the number of attributes associated with the supplementary index.

index_attribute_ID is the ID of an attribute within the same Table Data associated with the supplementary index.

index_type specifies the type of the supplementary index. Possible values include "CSI" (Crowd Sourced Indexing), "B-Tree", "R-Trees" and "LevelDB".

index_data is the indexing data on which queries by attribute values are performed to return the row and/or column indices of the matched data. The size of index_data is given by index_data_size=Length−[13+n_index_attributes×2+sizeof(index_type)], where Length is defined in the gen_info header of the tdsd container.

According to an embodiment, Table Data Master Index and Table Data Supplementary Indices can be grouped into one Annotation Table Indices data structure in an annotation table.

Table Data Block (Also Called Annotation Access Unit)

According to an embodiment, Table Data Block is a box containing the compressed payloads, either of the same chunk and ordered by attributes (block_type==0 for chunk contiguity), or of the same attribute and ordered by chunks (block_type==1 for attribute contiguity).

TABLE 20

Table Data Block Syntax

| Syntax | Key | Type |
|---|---|---|
| table_data_block { | tdbl | |
|   table_data_header | | table_data_header |
|   reserved | | u(7) |
|   block_type | | u(1) |
|   if (block_type == 0) { | | |
|     if (variable_size_chunks \|\| !two_dimensional) { | | |
|       chunk_idx_1 | | u(table_index_size*8) |
|       chunk_idx_2 = 0 | | |
|     } | | |
|     else { | | |
|       chunk_idx_1 | | u(table_index_size*8) |
|       chunk_idx_2 | | u(table_index_size*8) |
|     } | | |
|     for (i=0; i<n_attributes; i++) { | | |
|       payload_size[i][chunk_idx_1][chunk_idx_2] | | u(32) |
|       payload[i][chunk_idx_1][chunk_idx_2] | | u(payload_size[i]*8) |
|     } | | |
|   } | | |
|   else { | | |
|     attribute_ID | | u(16) |
|     if (variable_size_chunks \|\| !two_dimensional) { | | |
|       for (j=0; j<n_chunks; j++) { | | |
|         payload_size[attribute_ID][j] | | u(32) |
|         payload[attribute_ID][j] | | u(payload_size[i]*8) |
|       } | | |
|     } | | |
|     else if (column_major_chunk_order) { | | |
|       n_chunks_per_col | | u(table_index_size*8) |
|       for (k=0; k<n_chunks_per_row; k++) { | | |
|         for (j=0; j<n_chunks_per_col; j++) { | | |
|           payload_size[attribute_ID][j][k] | | u(32) |
|           payload[attribute_ID][j][k] | | u(payload_size[i]*8) |
|         } | | |
|       } | | |
|     } | | |
|     else { | | |
|       n_chunks_per_row | | u(table_index_size*8) |
|       for (j=0; j<n_chunks_per_col; j++) { | | |
|         for (k=0; k<n_chunks_per_row; k++) { | | |
|           payload_size[attribute_ID][j][k] | | u(32) |
|           payload[attribute_ID][j][k] | | u(payload_size[i]*8) |
|         } | | |
|       } | | |
|     } | | |
|   } | | |
| } | | |

According to an embodiment are the following Table Data Block semantics:

block_type is the type of the Table Data Block. The possible values are: 0=chunk-contiguous (consisting of payloads of different attributes belonging to the same chunk) and 1=attribute-contiguous (consisting of payloads of different chunks belonging to the same attribute).

(chunk_idx_1, chunk_idx_2) is the pair of row and column indices of the chunk associated with the Table Data Block, only applicable when block_type==0 (chunk-contiguous and implying same chunk structure across all attributes). When the Table Data is 2-d (two_dimensional==1) and a fixed chunk_size is applied (variable_size_chunks==0), the pair of indices starts from (0, 0) at the top-left of the Table Data, and increases by 1 for the next chunk towards the right/bottom. When the Table Data is 1-d (two_dimensional==0) or the chunk_size is variable (variable_size_chunks==1), only chunk_idx_1 is used and chunk_idx_2 is set to 0.

attribute_ID is the index of the attribute associated with the Table Data Block, only applicable when block_type==1 (attribute-contiguous). The attribute index, counting from 0, should be in the same order as the array of attribute_parameter_set in Table Data Attribute Information.

n_chunks_per_col specifies the total number of chunks in a column, only used when block_type==1 (attribute-contiguous), variable_size_chunks==0, two_dimensional==1 and column_major_chunk_order==1. This number is needed for computing the row and column indices of each chunk in the 2-d Table Data for data access and reconstruction.

n_chunks_per_row specifies the total number of chunks in a row, only used when block_type==1 (attribute-contiguous), variable_size_chunks==0, two_dimensional==1 and column_major_chunk_order==0. This number is needed for computing the row and column indices of each chunk in the 2-d Table Data for data access and reconstruction.

Note that the values of n_chunks, n_chunks_per_column and n_chunks_per_row are specific to the attribute referred to by attribute_ID if attribute_dependent_chunks==1.

(payload_size[i][j][k], payload[i][j][k]) are the size in number of bytes and data of the compressed payload that corresponds to the chunk of row and column indices (j, k) in the i-th attribute. Note that even for empty payloads, payload_size must be included and set to 0.

According to an embodiment, described below are data structures specific to the storage of genomic information.

Data Streams

According to an embodiment, a data stream is identified by a unique Stream_ID, equal to the SID field of packet header as specified herein, and it can transport any of the following data structures:

File Header: this data stream shall be unique and composed by one or more packets with Stream ID equal to 1,
Dataset Group Header,
Dataset Header,
Dataset Parameter Set,
Table Header,
Table Data Attribute Information,
Table Data Master Index,
Table Data Supplementary Indices,
Table Data Block,
data structures containing transport information (dataset mapping table list and dataset mapping table), and
metadata and protection information.

Dataset Mapping Table

According to an embodiment, Dataset Mapping Table is a mandatory box listing all data streams transporting data related to the dataset identified by dataset_ID. The syntax and semantics of Dataset Mapping Table remain the same as described elsewhere herein.

TABLE 21

Data_type Field Semantics

| data_type | Data structure |
| --- | --- |
| 0 | dataset_group_header |
| 3 | dataset_header |
| 4 | dataset_parameter_set |
| 5 | dataset_group_metadata |
| 6 | dataset_metadata |
| 7 | dataset_group_protection |
| 8 | dataset_protection |
| 15 | table_header |
| 16 | table_data_attribute_information |
| 17 | table_data_master_index |
| 18 | table_data_supplementary_indices |
| 19 | table_data_block |
| 20 | table_metadata |
| 21 | table_protection |

For the Table-related data types 15-21, it is recommended that their associated data_SID (Data Stream ID) be unique across different dataset_ID and dataset_group_ID for ease of implementation. However, the same data_SID can also be reused by the same data type of different dataset_ID and dataset_group_ID, provided the data structures are transported one after another in the same stream without interleaving of their packets, since the associated dataset_ID and dataset_group_ID are carried within the data structures. If data is generated by parallel processes, more than one data_SID can be assigned to data type 19 to speed up the transmission of Table Data Blocks, which carry the table payloads.

Table Data Header

According to an embodiment, Table Data Header is a mandatory data structure in the transport format for the four boxes—Table Data Attribute Information, Table Data Master Index, Table Data Supplementary Indices and Table Data Block—under Table Data. It contains the IDs of the upper-level containers that are required for the assembly of the Table Data structures after transport, but is excluded from the file format.

TABLE 22

Table Data Header Syntax

| Syntax | Key | Type |
| --- | --- | --- |
| table_data_header { | | |
| reserved | | u(5) |
| dataset_group_ID | | u(8) |
| dataset_ID | | u(16) |
| table_D | | u(8) |
| table_data_ID | | u(3) |
| } | | |

According to an embodiment are the following Table Data Header semantics:

dataset_group_ID is the identifier of dataset group containing the dataset identified by dataset_ID.

dataset_ID is the identifier of the dataset containing the Table identified by table_ID.

table_ID is the identifier of the table containing the Table Data identified by table_data_ID.

table_data_ID is the identifier of the Table Data containing the data structures associated with this Table Data Header.

Definitions

According to an embodiment, the following terms and definitions may apply. ISO and IEC maintain terminological databases for use in standardization.

Attribute—annotation data field that consists of one or multiple chunks on which the same compressor is applied. An attribute is defined in Table Data Attribute Parameter Set and identified by attribute ID unique within Table Data.

Attribute contiguity—setting for grouping payloads into Table Data Blocks by attribute and ordering them by chunk according to the choice of chunk order if Table Data is two dimensional.

Box—object-oriented building unit defined by a unique type identifier and length.

Chunk (or Tile)—rectangular region corresponding to specific ranges of rows and/or columns defined in Table Data Chunk Structure.

Chunk contiguity—setting for grouping payloads into Table Data Blocks by chunk and ordering them by attribute ID.

Chunk order—method of ordering chunks in two dimensional Table Data, can be either row-major, with elements arranged from left to right per row and then moving from one row to the next from top to bottom; or column-major, with elements arranged from top to bottom per column and then moving from one column to the next from left to right.

Compressor (or Compressor Parameter Set)—data structure within Dataset Parameter Set that contains configuration of transform and compression algorithms to be associated with one or more attributes through its unique Compressor ID within the annotation dataset.

Container box—box whose sole purpose is to contain and group a set of related boxes.

Data stream—set of packets transporting the same data type.

Dataset—container box identified by Dataset ID within Dataset Group that contains one or multiple Tables for the representation of genomic annotation data if Dataset Type is set to 3. The annotation data is further classified into subtypes that include "VCF", "GeneExpression", "Wig", "BigWig", "BedGraph", "BED", "GTF", "GFF", "GFF3", "GenBank", "HiC" and other user-defined values.

Dataset Mapping Table—mandatory box under Dataset that lists all data streams transporting data related to the dataset identified by Dataset ID.

Dataset Parameter Set—container box describing any of the parameter sets associated to the dataset. For annotation datasets, it contains the definition of compressors needed for the compression/decompression of attributes in tables.

File format—set of data structures for the storage of coded information.

Packet—transmission unit transporting segments of any of the data structures defined in this document.

Table (or Annotation Table)—container box in annotation dataset identified by Table ID and comprising tabulated annotation data that includes a main Table Data and optionally one or multiple auxiliary Table Data.

Table Data (or Attribute Group)—container box in Table identified by Table Data ID and grouping attributes into classes: 0—main; ½—auxiliary row/column data attributes; ¾—auxiliary row/column linkage attributes; 4-7—user-defined auxiliary attributes.

Table Data Attribute Information (or Attribute Information)—container box in Table Data that comprises a collection of attribute definitions encapsulated in Table Data Attribute Parameter Sets.

Table Data Attribute Parameter Set (or Attribute Parameter Set)—box in Table Data Attribute Information that contains the basic information of an attribute and its associated compressor.

Table Data Block (or Annotation Access Unit)—box in Table Data that groups and organizes the compressed payloads. There are two types of Table Data Block: Type 0 for chunk contiguity, where a block contains payloads of the same chunk ordered by their attribute IDs; and Type 1 for attribute contiguity, where a block contains payloads of the same attribute ordered by their chunk indices.

Table Data Byte Offset (or Attribute Data Byte Offset)—box in Table Data Master Index that comprises the byte-offset pointers to the Table Data Blocks and their individual payloads Table Data Chunk Structure (or Attribute Data Tile Structure)—box in Table Data Master Index that contains information on how Table Data should be divided into rectangular chunks. The chunk size, in term of number of rows/columns, can be uniform, in which case only the size per dimension needs to be specified, or variable, in which case the ranges of row and/or column indices need to be specified for individual chunks.

Table Data Header mandatory data structure in the transport format for the four boxes—Table Data Attribute Information, Table Data Master Index, Table Data Supplementary Indices and Table Data Block—in Table Data. It contains the IDs of the upper-level containers that are required for the assembly of the Table Data structures after transport, but is excluded from the file format.

Table Data Master Index (or Row-Column Index)—container box in Table Data that carries indexing information consisting of one or multiple (if attribute-dependent) Table Data Chunk Structure boxes, and a Table Data Byte Offset box. It enables the mapping between row and/or column indices of Table Data and specific chunks of an attribute.

Table Data Supplementary Indices—optional container box in Table Data that carries additional attribute-specific indexing data encapsulated in Table Data Supplementary Index Data for enabling query search based on criteria such as genomic region, gene symbol or any other attributes.

Table Data Supplementary Index Data (or Attribute Value Index)—box in Table Data Supplementary Indices that contains information and data of a supplementary index.

Transport format—set of data structures for the transport of coded information.

Variable—parameter either inferred from syntax fields or locally defined in a process description.

Mathematical Operators

The mathematical operators used herein are similar to those used in the C programming language. However, integer division with truncation and rounding are specifically defined. The bitwise operators are defined assuming two's-complement representation of integers. Numbering and counting loops generally begin from 0.

Arithmetic Operators

+ addition

− subtraction (as a binary operator) or negation (as a unary operator)

++ increment

* multiplication

/ integer division with truncation of the result toward 0
(for example, 7/4 and −7/−4 are truncated to 1 and −7/4 and 7/−4 are truncated to −1)

Logical Operators
|| logical OR
&& logical AND
! logical NOT

Relational Operators
> greater than
≥ greater than or equal to
< less than
≤ less than or equal to
== equal to
!= not equal to Bitwise Operators
& AND
| OR
>> shift right with sign extension
<< shift left with 0 fill Assignment
= assignment operator Unary Operators
sizeof(N) size in bytes of N, where N is either a data structure or a data type Indexing Capabilities According to an embodiment, indexing capabilities are realized through the following data structures:

(1) Table Data Master Index (or Row-Column Index) that provides the mapping between row and/or column indices of a table and specific chunks of an attribute.

(2) Table Data Supplementary Indices (or Attribute Value Indices) that provides the mapping between row and/or column indices of a table and values of selected attributes such as genomic position and gene symbols.

A compound query that consists of a logical combination of attribute conditions can be realized by (1) looking up the row and/or column indices satisfying each attribute condition independently, (2) identifying the subset of indices satisfying the logics in the compound query, (3) mapping the subset of indices to specific chunks of an attribute, and (4) looking up the locations of the payloads of the matching chunks.

Selective Access to Data Subsets

According to an embodiment, selective access is enabled through data chunking, i.e. dividing each table attribute into rectangular chunks, which are then compressed individually. To access data in specific regions of the table, the chunks or tiles in those regions are identified and their payloads located using the information in Table Data Master Index. Decompression is then applied only on the payloads of the matching chunks to retrieve the original data in the requested regions.

Controlled Access to and Authentication of Data Subsets

According to an embodiment, controlled access to and authentication of data subsets within a table in an annotation dataset are enabled through privacy rules and signature elements in the schema for Table Protection metadata. Users may define the attributes, chunks, genomic regions, and ranges of table indices on which a privacy rule is applied. There can be any number of XML signature elements in protection metadata and a URI should be used to specify the attributes and chunks associated with each signature.

Data Linkages

According to an embodiment, this format supports the creation of data linkages useful for join table query and efficient data visualization. Data linkages can be defined as URIs in:

(1) Table Metadata—at this level, linkages can be between two datasets, e.g. an annotation table and its originating sequencing dataset, or two tables, where the rows/columns of one table are mapped to the rows/columns of another table; and (2) Auxiliary Table Data (or auxiliary Attribute Group, classes 3 and 4) for row/column linkage attributes—at this level, a linkage is defined per row/column. For example, in a VCF file, each sample in the column should be linked to its corresponding sequencing dataset from which its variants are called.

Simplicity of Syntax

According to an embodiment, since this format for genomic annotation data is fully integrated into the MPEG-G container box hierarchy and uses the same data structures for transport, it can keep the syntax succinct by introducing only data structures specific to the organization of data within a table.

Flexibility

Flexibility is one of the main design principles of this format and is offered in the following aspects:

Customizable compressor configurations for adopting new transform and compression algorithms Customizable attribute definitions for accommodating new annotation file types Multiple Tables (or Annotation Tables) can be stored in a dataset, e.g. to represent data at different resolutions or time points Multiple auxiliary Table Data (or auxiliary Attribute Groups) can be provided to supplement the main Table Data (or main Attribute Group) with additional information Flexible chunk (or tile) structure—uniform or attribute-dependent, fixed- or variable-size—for optimum compression and random access performance Attribute or chunk (or tile) contiguity in grouping payloads into Table Data Blocks (or Annotation Access Units)

Row- or column-major chunk (or tile) order in organizing payloads or Table Data Blocks (or Annotation Access Units)

Different symmetry modes (0=unsymmetrical; 1=symmetrical; 2=skew-symmetric; 3=Hermitian; 4-7=reserved or user-defined) over the major/minor diagonal of a matrix Support for Future Extensions This format can be readily extended to accommodate any future annotation file types and transform/compression algorithms by providing new configurations of attributes and compressors defined in Table Data Attribute Information (or Attribute Information) and Dataset Parameter Set. This approach allows the building of generic software encoders/decoders, which obtain the instructions for processing the specific data by interpreting the attribute and compressor information explicitly defined through a uniform interface. Since the processing steps are not hardcoded, the required changes to the software for accommodating new data types are minimized.

Data Transport

Figure 11:
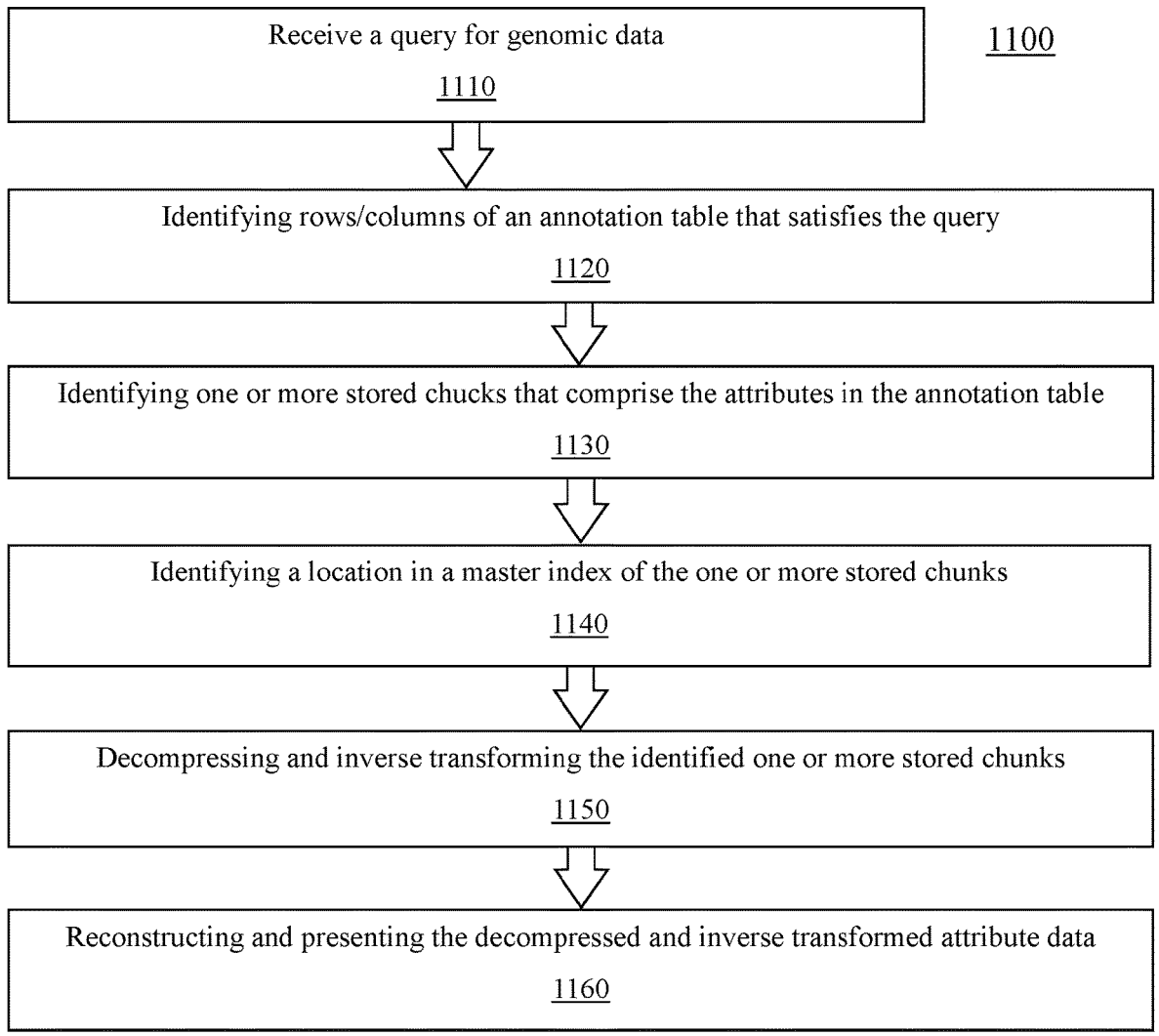
FIG. 11 is a flowchart of a method for decompressing stored genomic data, in accordance with an embodiment

According to an embodiment and referring to FIG. 11 is a flowchart of a method 1100 for reconstructing and presenting genomic data that has been compressed and stored as described or otherwise envisioned herein.

As step 1110 of the method, the data or file structure system receives a query for genomic data submitted on one or more annotation tables, the query based on a criterion such as a range of rows and columns, a genomic interval, a specific attribute, or other criteria. The query may be submitted by a user through a user interface, or via another system in communication with the file structure system.

At step 1120 of the method, the system identifies the rows and/or columns of the one or more annotation tables that satisfy the query criteria, using indexing data of the system. The indexing data may be, for example, the supplementary indices (or attribute value indices), genomic range indices or other indices.

At step 1130 of the method, the system identifies one or more stored and compressed chunks in the file structure that comprise data of one or more relevant attributes in the identified rows and/or columns of the annotation table.

At step 1140 of the method, the system looks up in a master index of the file structure system, a location of the identified one or more stored and compressed chunks in the file data structure.

At step 1150 of the method, the system decompresses and inverse transforms each of the identified one or more stored and compressed. According to an embodiment, the decompression and inverse transformation is based on the compressor parameter set associated with each attribute.

At step 1160 of the method, the system reconstructs and presents the decompressed attribute data based on the attribute information and/or some output template that provides formatting instructions.

Figure 12:
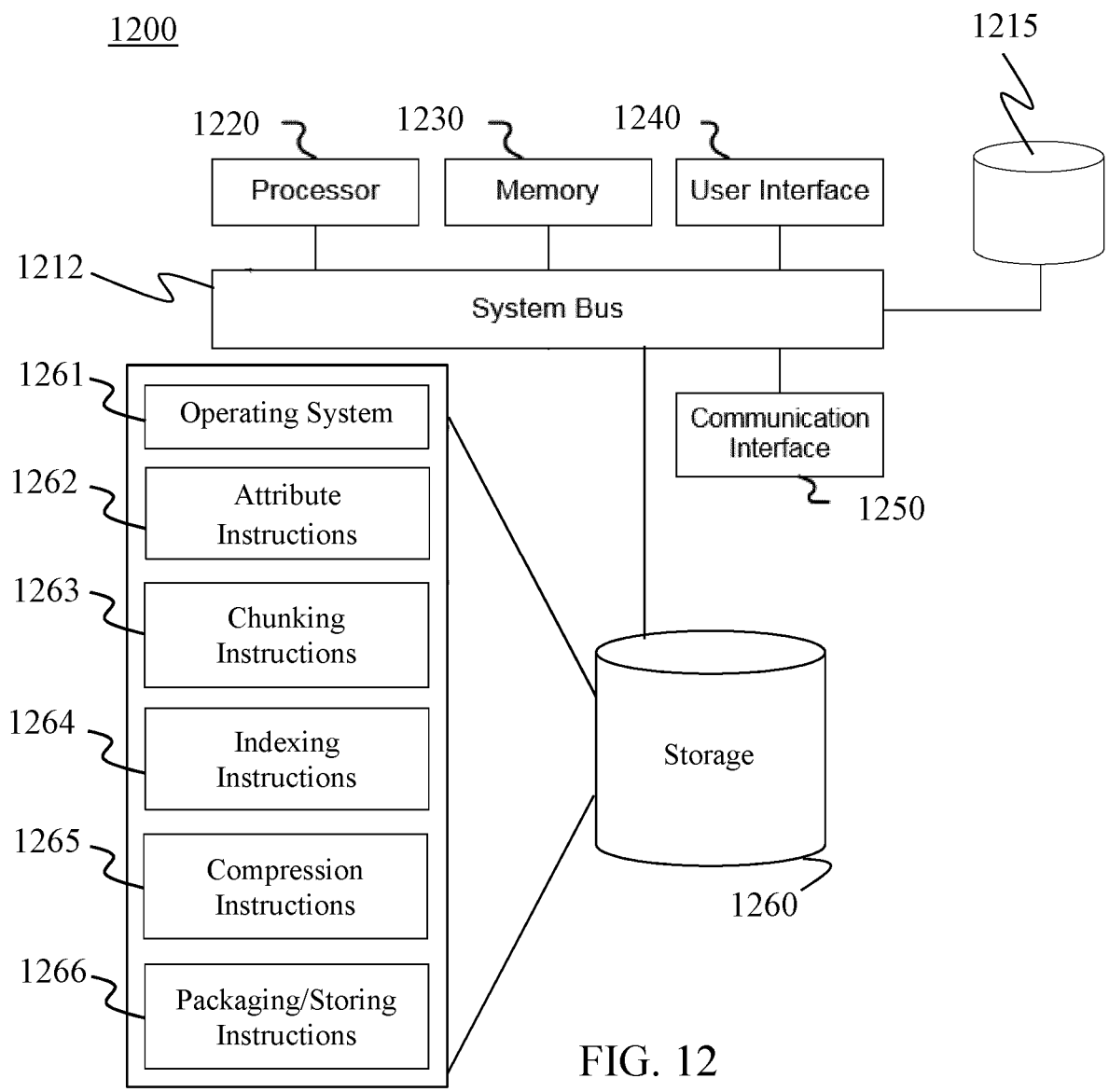
FIG. 12 is a schematic representation of a genomic data storage system, in accordance with an embodiment.

Referring to FIG. 12, in one embodiment, is a schematic representation of a system 1200 for storing genomic data. System 1200 may be any of the systems described or otherwise envisioned herein, and may comprise any of the components described or otherwise envisioned herein.

According to an embodiment, system 1200 comprises one or more of a processor 1220, memory 1230, user interface 1240, communications interface 1250, and storage 1260, interconnected via one or more system buses 1212. In some embodiments, the hardware may include a genomic data database 1215. It will be understood that FIG. 12 constitutes, in some respects, an abstraction and that the actual organization of the components of the system 1200 may be different and more complex than illustrated.

According to an embodiment, system 1200 comprises a processor 1220 capable of executing instructions stored in memory 1230 or storage 1260 or otherwise processing data to, for example, perform one or more steps of the method. Processor 1220 may be formed of one or multiple modules. Processor 1220 may take any suitable form, including but not limited to a microprocessor, microcontroller, multiple microcontrollers, circuitry, field programmable gate array (FPGA), application-specific integrated circuit (ASIC), a single processor, or plural processors.

Memory 1230 can take any suitable form, including a non-volatile memory and/or RAM. The memory 1230 may include various memories such as, for example L1, L2, or L3 cache or system memory. As such, the memory 1230 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 1200. It will be apparent that, in embodiments where the processor implements one or more of the functions described herein in hardware, the software described as corresponding to such functionality in other embodiments may be omitted.

User interface 1240 may include one or more devices for enabling communication with a user. The user interface can be any device or system that allows information to be conveyed and/or received, and may include a display, a mouse, and/or a keyboard for receiving user commands. In some embodiments, user interface 1240 may include a command line interface or graphical user interface that may be presented to a remote terminal via communication interface 1250. The user interface may be located with one or more other components of the system, or may located remote from the system and in communication via a wired and/or wireless communications network.

Communication interface 1250 may include one or more devices for enabling communication with other hardware devices. For example, communication interface 1250 may include a network interface card (MC) configured to communicate according to the Ethernet protocol. Additionally, communication interface 1250 may implement a TCP/IP stack for communication according to the TCP/IP protocols. Various alternative or additional hardware or configurations for communication interface 1250 will be apparent.

Storage 1260 may include one or more machine-readable storage media such as read-only memory (ROM), random-access memory (RANI), magnetic disk storage media, optical storage media, flash-memory devices, or similar storage media. In various embodiments, storage 1260 may store instructions for execution by processor 1220 or data upon which processor 1220 may operate. For example, storage 1260 may store an operating system 1261 for controlling various operations of system 1200.

It will be apparent that various information described as stored in storage 1260 may be additionally or alternatively stored in memory 1230. In this respect, memory 1230 may also be considered to constitute a storage device and storage 1260 may be considered a memory. Various other arrangements will be apparent. Further, memory 1230 and storage 1260 may both be considered to be non-transitory machine-readable media. As used herein, the term non-transitory will be understood to exclude transitory signals but to include all forms of storage, including both volatile and non-volatile memories.

While system 1200 is shown as including one of each described component, the various components may be duplicated in various embodiments. For example, processor 1220 may include multiple microprocessors that are configured to independently execute the methods described herein or are configured to perform steps or subroutines of the methods described herein such that the multiple processors cooperate to achieve the functionality described herein. Further, where one or more components of system 1200 is implemented in a cloud computing system, the various hardware components may belong to separate physical systems. For example, processor 1220 may include a first processor in a first server and a second processor in a second server. Many other variations and configurations are possible.

According to an embodiment, storage 1260 of system 1200 may store one or more algorithms and/or instructions to carry out one or more functions or steps of the methods described or otherwise envisioned herein. For example, processor 1220 may comprise one or more of attribute instructions 1262, chunking instructions 1263, indexing instructions 1264, compression/decompression instructions 1265, and/or storage instructions 1266, among other instructions.

According to an embodiment, attribute instructions 1262 direct the system to extract attributes from the genomic dataset. An attribute can be any data element or characteristic defined by or contained within the data type. For example, attributes of genomic data may be a chromosome number, a position along a chromosome, an RSID, a reference value, a sequencing result, a quality score or value, a gene expression value, a functional annotation, or any of a wide variety of other attributes. This non-exhaustive list is understood not to be limiting, and that attributes can be created and defined as needed. Attributes will depend at least in part on the type of genomic data received or processed by the genomic data storage system.

According to an embodiment, chunking instructions 1263 direct the system to break attributes into smaller chunks of a predetermined size. For example, a chunk can be a rectangular region of a table corresponding to specific ranges of rows and/or columns. Accordingly, the master index may comprise information on how attribute table data should be divided into rectangular chunks. The chunk size, in term of number of rows/columns, can be uniform in which case only the size per dimension needs to be specified, or variable, in which case the ranges of row and/or column indices need to be specified for individual chunks. Often, the same chunk structure is applied to all attributes for ease of indexing. However, in cases where the attributes have widely different characteristics, attribute-dependent chunk structures can be applied. In general, a larger chunk size improves the compression ratio but reduces the speed of selective access.

According to an embodiment, indexing instructions 1264 direct the system to index each of the plurality of chunks in a master index of the data structure. The master index includes lookup data for each of the plurality of chunks. For example, the master index can comprise row and/or column indices that specify individual chunks.

According to an embodiment, compression/decompression instructions 1265 direct the system to compress each of the plurality of chunks individual and independently using a compression algorithm. The compression algorithm can be any algorithm, method, or process for data compression. By compressing each chunk individual and independently, data can be more rapidly accessed as small individual chunks can be accessed and decompressed when needed. The compression instructions may also comprise decompression instructions for decompression stored data.

According to an embodiment, storage instructions 1266 direct the system to store each compressed chunk within an allocated location within a chunk table of the data structure, as defined by the master index. Accordingly, the data structure is configured such that each of the plurality of chunks can be decompressed individually.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for packaging genomic data within a file structure, the method comprising:
receiving a genomic dataset comprising genomic data of one of a plurality of different types of genomic data;
extracting a plurality of attributes from the genomic dataset, wherein each of the plurality of attributes is defined within an attribute information data structure;
breaking each attribute into a plurality of chunks of a predetermined size, wherein the predetermined size of a chunk is defined within a master index of the data structure;
indexing each of the plurality of chunks in the master index of the data structure, the master index comprising lookup data for each of the plurality of chunks;
compressing, with transform and compression algorithms, each of the plurality of chunks individually; and
packaging each compressed chunk within an allocated location within a table block of the data structure, as defined by the master index;
wherein the data structure is configured such that each of the plurality of chunks can be decompressed individually,
wherein for each of the genomic data types, the definition of attributes, the definition of chunk size, the transform and compression algorithms, and the organization of chunks can be modified without changing the file structure,
wherein the plurality of attributes are one-dimensional attributes, two-dimensional attributes, or a combination thereof, and further wherein parameters of the plurality of attributes and the associated transform and compression algorithms are defined by a uniform interface consisting of Attribute Information, Attribute Parameter Set, and Compressor Parameter Set data structures,
wherein a symmetry mode of data for each of the genomic data types can be modified without changing the file structure,
wherein the symmetry mode is selected from a set of different symmetry modes, and
wherein the set of different symmetry modes comprises an unsymmetrical mode, a symmetrical mode, a skew-symmetric mode, and a Hermitian mode.

2. The method of claim 1, wherein a Compressor Parameter Set definition can enable:
a sparse transform configured to convert a data matrix into streams of coordinates and values only of entries with non-default values;
an attribute-dependent transform requiring values of one or multiple attributes; and
application of a single or a cascade of compression algorithms with their corresponding parameters.

3. The method of claim 1, wherein the data structure further comprises:
one or more annotation tables representing data at multiple resolutions or time points;
a main attribute group; and
one or more auxiliary attribute groups comprising different functional classes and populated with auxiliary data, the auxiliary data comprising additional attributes or additional information about the extracted plurality of attributes in a main attribute group.

4. The method of claim 1, wherein the data structure further comprises a supplementary index configured to facilitate query by values of specific attributes.

5. The method of claim 1, wherein chunks are organized within the annotation access units of the file structure based on the extracted plurality of attributes, wherein grouping and/or ordering of the with the grouping and ordering of the chunks is customizable through variables such as attribute_contiguity and column_major_chunk_order.

6. The method of claim 1, wherein each chunk is a region of an annotation table corresponding to a specific range of rows and/or columns of the annotation table.

7. The method of claim 1, wherein one or more of the plurality of attributes, the predetermined size of the plurality of chunks, and the associated transform and compression algorithms for each attribute is determined by a user or a software algorithm.

8. The method of claim 1, wherein the set of different symmetry modes comprises at least one of an unsymmetrical classification, a symmetrical classification, a skew-symmetric classification, a Hermitian classification, a reserved classification, or a user-defined classification.

9. A system for packaging genomic data, the system comprising:
a genomic dataset comprising genomic data of one of a plurality of different types of genomic data;
a data structure configured to store genomic data;
a data compression algorithm; and
a processor configured to: (i) extract a plurality of attributes from the genomic dataset, wherein each of the plurality of attributes is defined within an attribute information table of the data structure; (ii) break each attribute into a plurality of chunks of a predetermined size, wherein the predetermined size of a chunk is defined within a master index of the data structure; (iii) index each of the plurality of chunks in the master index of the data structure, the master index comprising lookup data for each of the plurality of chunks; (iv) compressing, with a transform algorithm and the data compression algorithm, each of the plurality of chunks individually; and (v) package each compressed chunk within an allocated location within a chunk table of the data structure, as defined by the master index;
wherein the data structure is configured such that each of the plurality of chunks can be decompressed individually,
wherein for each of the genomic data types, the definition of attributes, the definition of chunk size, the transform and compression algorithms, and the organization of chucks can be modified without changing either the data structure,
wherein the plurality of attributes are one-dimensional attributes, two-dimensional attributes, or a combination thereof, and further wherein the parameters of the plurality of attributes and the associated transform and compression algorithms are defined by a uniform interface consisting of Attribute Information, Attribute Parameter Set, and Compressor Parameter Set data structures,
wherein a symmetry mode of data for each of the genomic data types can be modified without changing the file structure,
wherein the symmetry mode is selected from a set of different symmetry modes, and
wherein the set of different symmetry modes comprises an unsymmetrical mode, a symmetrical mode, a skew-symmetric mode, and a Hermitian mode.

10. The system of claim 9, wherein a compressor parameter set definition can enable:
- a sparse transform configured to convert a data matrix into streams of coordinates and values only of entries with non-default values;
- an attribute-dependent transform requiring values of one or multiple attributes; and
- application of a single or a cascade of compression algorithms with their corresponding parameters.

11. The system of claim 9, wherein the data structure further comprises:
- one or more annotation tables representing data at multiple resolutions or time points;
- a main attribute group; and
- one or more auxiliary attribute groups comprising different functional classes and populated with auxiliary data, the auxiliary data comprising additional attributes or additional information about the extracted plurality of attributes in a main attribute group.

12. The system of claim 9, wherein chunks are organized within the annotation access units of the data structure based on the extracted plurality of attributes, wherein grouping and/or ordering of the with the grouping and ordering of the chunks is customizable through variables such as attribute_contiguity and column_major_chunk_order.

13. The method of claim 9, wherein the set of different symmetry modes comprises at least one of an unsymmetrical classification, a symmetrical classification, a skew-symmetric classification, a Hermitian classification, a reserved classification, or a user-defined classification.

* * * * *